US010206701B2

(12) United States Patent
Conlon et al.

(10) Patent No.: US 10,206,701 B2
(45) Date of Patent: Feb. 19, 2019

(54) COMPOUND ANGLE LAPAROSCOPIC METHODS AND DEVICES

(71) Applicant: Ethicon Endo-Surgery, Inc., Cincinnati, OH (US)

(72) Inventors: Sean P. Conlon, Loveland, OH (US); William B. Weisenburgh, II, Maineville, OH (US)

(73) Assignee: Ethicon LLC, Guaynabo, PR (US)

(*) Notice: Subject to any disclaimer, the term of this patent is extended or adjusted under 35 U.S.C. 154(b) by 75 days.

(21) Appl. No.: 15/267,750

(22) Filed: Sep. 16, 2016

(65) Prior Publication Data

US 2017/0000507 A1 Jan. 5, 2017

Related U.S. Application Data

(63) Continuation of application No. 14/032,747, filed on Sep. 20, 2013, now Pat. No. 9,468,426, which is a
(Continued)

(51) Int. Cl.
*A61B 17/29* (2006.01)
*A61B 17/00* (2006.01)
(Continued)

(52) U.S. Cl.
CPC ........ *A61B 17/29* (2013.01); *A61B 17/00234* (2013.01); *A61B 17/3421* (2013.01);
(Continued)

(58) Field of Classification Search
CPC .............. A61B 17/29; A61B 17/00234; A61B 17/3423; A61B 17/3421
See application file for complete search history.

(56) References Cited

U.S. PATENT DOCUMENTS 2,765,930 A   10/1956   Geer et al.
3,402,710 A    9/1968   Paleschuck
(Continued)

FOREIGN PATENT DOCUMENTS

DE   4300307 A1   7/1994
DE   4324254 C1   1/1995
(Continued)

OTHER PUBLICATIONS

"1 Lap Disc Hand Access Device—Ref. Ld111," by Ethicon Endo-Surgery, Inc. (date unknown but no later than May 15, 2007, date of citation in U.S. Appl. No. 11/398,985; 1 page).
(Continued)

*Primary Examiner* — Richard Louis
(74) *Attorney, Agent, or Firm* — Mintz Levin Cohn Ferris Glovsky and Popeo, P.C.

(57) ABSTRACT

Methods and devices are provided for performing minimally invasive surgical procedures. In one embodiment, a surgical device is provided that include an elongate shaft having a distal portion configured to be movable between a first configuration in which the distal portion of the shaft is substantially straight or linear and a second configuration in which the distal portion of the shaft is articulated at a compound angle. The shaft's distal portion can include two articulation joints to facilitate formation of the compound angle.

14 Claims, 10 Drawing Sheets

Related U.S. Application Data continuation of application No. 12/775,724, filed on May 7, 2010, now Pat. No. 8,562,592.

(51) Int. Cl.
   *A61B 17/34* (2006.01)
   *A61B 17/28* (2006.01)
   *A61B 90/00* (2016.01)

(52) U.S. Cl.
   CPC .......... *A61B 17/3423* (2013.01); *A61B 17/28* (2013.01); *A61B 2017/00367* (2013.01); *A61B 2017/00738* (2013.01); *A61B 2017/2905* (2013.01); *A61B 2017/2906* (2013.01); *A61B 2017/2908* (2013.01); *A61B 2017/2927* (2013.01); *A61B 2017/3466* (2013.01); *A61B 2090/035* (2016.02)

(56) References Cited

U.S. PATENT DOCUMENTS

| | | |
|---|---|---|
| 3,503,396 A | 3/1970 | Pierie et al. |
| 3,654,965 A | 4/1972 | Gramain |
| 4,041,931 A | 8/1977 | Elliott et al. |
| 4,048,987 A | 9/1977 | Hurson |
| 4,112,932 A | 9/1978 | Chiulli |
| 4,120,302 A | 10/1978 | Ziegler |
| 4,203,430 A | 5/1980 | Takahashi |
| 4,306,545 A | 12/1981 | Ivan et al. |
| 4,373,532 A | 2/1983 | Hill et al. |
| 2,129,391 A | 9/1983 | Frederick |
| 4,402,683 A | 9/1983 | Kopman |
| 4,417,888 A | 11/1983 | Cosentino et al. |
| 4,559,947 A | 12/1985 | Renger et al. |
| 4,608,977 A | 9/1986 | Brown |
| 4,669,473 A | 6/1987 | Richards et al. |
| 4,821,719 A | 4/1989 | Fogarty |
| 4,831,070 A | 5/1989 | McInally et al. |
| 4,880,015 A | 11/1989 | Nierman |
| 5,020,514 A | 6/1991 | Heckele |
| 5,027,800 A | 7/1991 | Rowland |
| 5,058,603 A | 10/1991 | Doi et al. |
| 5,141,498 A | 8/1992 | Christian |
| 5,183,471 A | 2/1993 | Wilk |
| 5,197,955 A | 3/1993 | Stephens et al. |
| 5,201,742 A | 4/1993 | Hasson |
| 5,207,213 A | 5/1993 | Auhll et al. |
| 5,209,737 A | 5/1993 | Ritchart et al. |
| 5,209,741 A | 5/1993 | Spaeth |
| 5,209,747 A | 5/1993 | Knoepfler |
| 5,269,772 A | 12/1993 | Wilk |
| 5,275,614 A | 1/1994 | Haber et al. |
| 5,284,128 A | 2/1994 | Hart |
| 5,308,336 A | 5/1994 | Hart et al. |
| 5,312,023 A | 5/1994 | Green et al. |
| 5,329,923 A | 7/1994 | Lundquist |
| 5,330,437 A | 7/1994 | Durman |
| 5,330,502 A | 7/1994 | Hassler et al. |
| 5,342,396 A | 8/1994 | Cook |
| 5,345,927 A | 9/1994 | Bonutti |
| 5,350,391 A | 9/1994 | Iacovelli |
| 5,360,428 A | 11/1994 | Hutchinson, Jr. |
| 5,362,294 A | 11/1994 | Seitzinger |
| 5,366,478 A | 11/1994 | Brinkerhoff et al. |
| 5,368,597 A | 11/1994 | Pagedas |
| 5,374,277 A | 12/1994 | Hassler |
| 5,381,943 A | 1/1995 | Allen et al. |
| 5,383,888 A | 1/1995 | Zvenyatsky et al. |
| 5,385,553 A | 1/1995 | Hart et al. |
| 5,385,560 A | 1/1995 | Wulf |
| 5,391,154 A | 2/1995 | Young |
| 5,398,617 A | 3/1995 | Deandrea |
| 5,403,342 A | 4/1995 | Tovey et al. |
| 5,417,203 A | 5/1995 | Tovey et al. |
| 5,419,339 A | 5/1995 | Palmer |
| 5,441,483 A | 8/1995 | Avitall |
| 5,443,452 A | 8/1995 | Hart et al. |
| 5,443,484 A | 8/1995 | Kirsch et al. |
| 5,445,648 A | 8/1995 | Cook |
| 5,456,684 A | 10/1995 | Schmidt et al. |
| 5,480,410 A | 1/1996 | Cuschieri et al. |
| 5,489,256 A | 2/1996 | Adair |
| 5,489,290 A | 2/1996 | Furnish |
| 5,501,653 A | 3/1996 | Chin |
| 5,514,157 A | 5/1996 | Nicholas et al. |
| 5,520,609 A | 5/1996 | Moll et al. |
| 5,520,678 A | 5/1996 | Heckele et al. |
| 5,545,123 A | 8/1996 | Ortiz et al. |
| 5,545,179 A | 8/1996 | Williamson, IV |
| 5,547,458 A | 8/1996 | Ortiz et al. |
| 5,549,637 A | 8/1996 | Crainich |
| 5,569,205 A | 10/1996 | Hart et al. |
| 5,569,254 A | 10/1996 | Carlson et al. |
| 5,571,090 A | 11/1996 | Sherts |
| 5,571,129 A | 11/1996 | Porter |
| 5,573,520 A | 11/1996 | Schwartz et al. |
| 5,578,048 A | 11/1996 | Pasqualucci et al. |
| 5,582,577 A | 12/1996 | Lund et al. |
| 5,582,617 A | 12/1996 | Klieman et al. |
| 5,584,850 A | 12/1996 | Hart et al. |
| 5,586,977 A | 12/1996 | Dorsey, III |
| 5,591,182 A | 1/1997 | Johnson |
| 5,595,193 A | 1/1997 | Walus et al. |
| 5,607,450 A | 3/1997 | Zvenyatsky et al. |
| 5,609,601 A | 3/1997 | Kolesa et al. |
| 5,618,291 A | 4/1997 | Thompson et al. |
| 5,618,294 A | 4/1997 | Aust et al. |
| 5,624,381 A | 4/1997 | Kieturakis |
| 5,626,608 A | 5/1997 | Cuny et al. |
| 5,630,831 A | 5/1997 | Lahr |
| 5,632,432 A | 5/1997 | Schulze et al. |
| 5,632,734 A | 5/1997 | Galel et al. |
| 5,634,882 A | 6/1997 | Gagner |
| 5,634,883 A | 6/1997 | Chin et al. |
| 5,634,911 A | 6/1997 | Hermann et al. |
| 5,634,937 A | 6/1997 | Mollenauer et al. |
| 5,636,645 A | 6/1997 | Ou |
| 5,640,977 A | 6/1997 | Leahy et al. |
| 5,643,283 A | 7/1997 | Younker |
| 5,643,301 A | 7/1997 | Mollenauer |
| 5,647,372 A | 7/1997 | Tovey et al. |
| 5,653,705 A | 8/1997 | de la Torre et al. |
| 5,665,093 A | 9/1997 | Atkins et al. |
| 5,667,527 A | 9/1997 | Cook |
| 5,672,168 A | 9/1997 | de la Torre et al. |
| 5,676,146 A | 10/1997 | Scarborough |
| 5,676,657 A | 10/1997 | Yoon |
| 5,681,324 A | 10/1997 | Kammerer et al. |
| 5,695,448 A | 12/1997 | Kimura et al. |
| 5,700,275 A | 12/1997 | Bell et al. |
| 5,704,534 A | 1/1998 | Huitema et al. |
| 5,713,919 A | 2/1998 | Lahr |
| 5,716,327 A | 2/1998 | Warner et al. |
| 5,716,407 A | 2/1998 | Knapp et al. |
| 5,728,121 A | 3/1998 | Bimbo et al. |
| 5,735,289 A | 4/1998 | Pfeffer et al. |
| 5,743,456 A | 4/1998 | Jones et al. |
| 5,743,851 A | 4/1998 | Moll et al. |
| 5,766,205 A | 6/1998 | Zvenyatsky et al. |
| 5,772,654 A | 6/1998 | Leyva |
| 5,782,812 A | 7/1998 | Hart et al. |
| 5,782,859 A | 7/1998 | Nicholas et al. |
| 5,792,165 A | 8/1998 | Klieman et al. |
| 5,797,959 A | 8/1998 | Castro et al. |
| 5,803,919 A | 9/1998 | Hart et al. |
| 5,813,409 A | 9/1998 | Leahy et al. |
| 5,814,058 A | 9/1998 | Carlson et al. |
| 5,816,257 A | 10/1998 | Chin |
| 5,827,319 A | 10/1998 | Carlson et al. |
| 5,827,323 A | 10/1998 | Klieman et al. |
| 5,833,692 A | 11/1998 | Cesarini et al. |
| 5,836,960 A | 11/1998 | Kolesa et al. |
| 5,840,078 A | 11/1998 | Yerys |
| 5,853,395 A | 12/1998 | Crook et al. |

(56) References Cited

U.S. PATENT DOCUMENTS

| | | |
|---|---|---|
| 5,865,807 A | 2/1999 | Blake, III |
| 5,872,859 A | 2/1999 | Gur et al. |
| 5,876,447 A | 3/1999 | Arnett |
| 5,891,013 A | 4/1999 | Thompson |
| 5,893,878 A | 4/1999 | Pierce |
| 5,906,577 A | 5/1999 | Beane et al. |
| 5,921,956 A | 7/1999 | Grinberg et al. |
| 5,941,890 A | 8/1999 | Voegele et al. |
| 5,947,922 A | 9/1999 | MacLeod |
| 5,957,913 A | 9/1999 | de la Torre et al. |
| 5,971,995 A | 10/1999 | Rousseau |
| 5,977,431 A | 11/1999 | Knapp et al. |
| 5,990,382 A | 11/1999 | Fox |
| 6,007,561 A | 12/1999 | Bourque et al. |
| 6,024,708 A | 2/2000 | Bales et al. |
| 6,024,736 A | 2/2000 | de la Torre et al. |
| 6,027,522 A | 2/2000 | Palmer |
| 6,033,428 A | 3/2000 | Sardella |
| RE36,702 E | 5/2000 | Green et al. |
| 6,074,419 A | 6/2000 | Healy et al. |
| 6,077,287 A | 6/2000 | Taylor et al. |
| 6,077,288 A | 6/2000 | Shimomura et al. |
| 6,086,603 A | 7/2000 | Termin et al. |
| 6,093,141 A | 7/2000 | Mosseri et al. |
| 6,110,154 A | 8/2000 | Shimomura et al. |
| 6,110,182 A | 8/2000 | Mowlai-Ashtiani |
| 6,120,513 A | 9/2000 | Bailey et al. |
| 6,123,689 A | 9/2000 | To et al. |
| 6,126,671 A | 10/2000 | Richards et al. |
| 6,132,385 A | 10/2000 | Vain |
| 6,149,642 A | 11/2000 | Gerhart et al. |
| 6,156,045 A | 12/2000 | Ulbrich et al. |
| 6,156,184 A | 12/2000 | Antonucci et al. |
| 6,159,200 A | 12/2000 | Verdura et al. |
| 6,162,196 A | 12/2000 | Hart et al. |
| 6,162,208 A | 12/2000 | Hipps |
| 6,165,184 A | 12/2000 | Verdura et al. |
| 6,171,282 B1 | 1/2001 | Ragsdale |
| 6,197,034 B1 | 3/2001 | Gvozdic et al. |
| 6,217,555 B1 | 4/2001 | Hart et al. |
| 6,220,248 B1 | 4/2001 | Voegele et al. |
| 6,228,055 B1 | 5/2001 | Foerster et al. |
| 6,245,011 B1 | 6/2001 | Dudda et al. |
| 6,245,052 B1 | 6/2001 | Orth et al. |
| 6,248,062 B1 | 6/2001 | Adler et al. |
| 6,258,069 B1 | 7/2001 | Carpentier et al. |
| 6,258,102 B1 | 7/2001 | Pagedas |
| 6,261,302 B1 | 7/2001 | Voegele et al. |
| 6,264,599 B1 | 7/2001 | Slater et al. |
| 6,290,705 B1 | 9/2001 | Chan et al. |
| 6,293,966 B1 | 9/2001 | Frantzen |
| 6,315,770 B1 | 11/2001 | de la Torre et al. |
| 6,319,246 B1 | 11/2001 | de la Torre et al. |
| 6,347,940 B1 | 2/2002 | Gordils Wallis et al. |
| 6,348,034 B1 | 2/2002 | Thompson |
| 6,352,503 B1 | 3/2002 | Matsui et al. |
| 6,400,979 B1 | 6/2002 | Stoianovici et al. |
| 6,402,687 B1 | 6/2002 | Ouchi |
| 6,425,903 B1 | 7/2002 | Voegele |
| 6,443,960 B1 | 9/2002 | Brabrand et al. |
| 6,447,443 B1 | 9/2002 | Keogh et al. |
| 6,447,489 B1 | 9/2002 | Peterson |
| 6,454,783 B1 | 9/2002 | Piskun |
| 6,456,184 B1 | 9/2002 | Vu et al. |
| 6,458,077 B1 | 10/2002 | Boebel et al. |
| 6,471,714 B1 | 10/2002 | Kim |
| 6,485,467 B1 | 11/2002 | Crook et al. |
| 6,494,211 B1 | 12/2002 | Boyd et al. |
| 6,551,270 B1 | 4/2003 | Bimbo et al. |
| 6,551,282 B1 | 4/2003 | Exline et al. |
| 6,578,577 B2 | 6/2003 | Bonadio et al. |
| 6,579,304 B1 | 6/2003 | Hart et al. |
| 6,589,167 B1 | 7/2003 | Shimomura et al. |
| 6,605,063 B2 | 8/2003 | Bousquet |
| 6,613,068 B2 | 9/2003 | Ouchi |
| 6,623,426 B2 | 9/2003 | Bonadio et al. |
| 6,634,883 B2 | 10/2003 | Ranalli |
| RE38,335 E | 11/2003 | Aust et al. |
| 6,663,641 B1 | 12/2003 | Kovac et al. |
| 6,665,554 B1 | 12/2003 | Charles et al. |
| 6,666,854 B1 | 12/2003 | Lange |
| 6,669,674 B1 | 12/2003 | Macoviak et al. |
| 6,673,092 B1 | 1/2004 | Bacher |
| 6,689,122 B2 | 2/2004 | Yamamoto |
| 6,706,033 B1 | 3/2004 | Martinez et al. |
| 6,706,050 B1 | 3/2004 | Giannadakis |
| 6,725,083 B1 | 4/2004 | Burbank et al. |
| 6,764,473 B2 | 7/2004 | Morton |
| 6,766,186 B1 | 7/2004 | Hoyns et al. |
| 6,807,965 B1 | 10/2004 | Hickle |
| 6,810,880 B1 | 11/2004 | Jennings, Jr. et al. |
| 6,818,007 B1 | 11/2004 | Dampney et al. |
| 6,821,247 B2 | 11/2004 | Vierra et al. |
| 6,846,287 B2 | 1/2005 | Bonadio et al. |
| 6,872,433 B2 | 3/2005 | Seward et al. |
| 6,908,430 B2 | 6/2005 | Caldwell et al. |
| 6,913,613 B2 | 7/2005 | Schwarz et al. |
| 6,936,061 B2 | 8/2005 | Sasaki |
| 6,939,296 B2 | 9/2005 | Ewers et al. |
| 6,945,932 B1 | 9/2005 | Caldwell et al. |
| 6,966,876 B2 | 11/2005 | Irion et al. |
| 6,972,026 B1 | 12/2005 | Caldwell et al. |
| 6,994,712 B1 | 2/2006 | Fisher et al. |
| 7,008,377 B2 | 3/2006 | Beane et al. |
| 7,014,628 B2 | 3/2006 | Bousquet |
| 7,021,173 B2 | 4/2006 | Stoianovici et al. |
| 7,047,063 B2 | 5/2006 | Burbank et al. |
| 7,052,454 B2 | 5/2006 | Taylor |
| 7,083,576 B2 | 8/2006 | Zarins et al. |
| 7,083,626 B2 | 8/2006 | Hart et al. |
| 7,087,071 B2 | 8/2006 | Nicholas et al. |
| 7,118,528 B1 | 10/2006 | Piskun |
| 7,147,650 B2 | 12/2006 | Lee |
| 7,163,510 B2 | 1/2007 | Kahle et al. |
| 7,201,734 B2 | 4/2007 | Hickle |
| 7,208,005 B2 | 4/2007 | Frecker et al. |
| 7,214,185 B1 | 5/2007 | Rosney et al. |
| 7,247,154 B2 | 7/2007 | Hickle |
| 7,311,661 B2 | 12/2007 | Heinrich |
| 7,331,661 B2 | 2/2008 | Silverbrook et al. |
| 7,331,750 B2 | 2/2008 | Merz et al. |
| 7,338,473 B2 | 3/2008 | Campbell et al. |
| 7,344,547 B2 | 3/2008 | Piskun |
| 7,347,862 B2 | 3/2008 | Layer |
| 7,416,533 B2 | 8/2008 | Gellman et al. |
| 7,615,005 B2 | 11/2009 | Stefanchik et al. |
| 7,691,095 B2 | 4/2010 | Bednarek et al. |
| 7,909,220 B2 | 3/2011 | Viola |
| 7,985,239 B2 | 7/2011 | Suzuki |
| 7,988,699 B2 | 8/2011 | Martz et al. |
| 8,083,667 B2 | 12/2011 | Cooper et al. |
| 8,182,418 B2 | 5/2012 | Durant et al. |
| 8,562,592 B2 | 10/2013 | Conlon et al. |
| 8,758,232 B2 | 6/2014 | Graham et al. |
| 8,821,388 B2 | 9/2014 | Naito et al. |
| 9,226,760 B2 | 1/2016 | Shelton, IV |
| 9,333,001 B2 | 5/2016 | Stokes et al. |
| 9,468,426 B2 | 10/2016 | Conlon et al. |
| 9,474,540 B2 | 10/2016 | Stokes et al. |
| 2001/0034528 A1 | 10/2001 | Foerster et al. |
| 2001/0053510 A1 | 12/2001 | Ranalli |
| 2002/0007112 A1 | 1/2002 | Rupp et al. |
| 2002/0026201 A1 | 2/2002 | Foerster et al. |
| 2002/0103434 A1 | 8/2002 | Swanbom |
| 2002/0156432 A1 | 10/2002 | Racenet et al. |
| 2002/0156497 A1 | 10/2002 | Nagase et al. |
| 2002/0173805 A1 | 11/2002 | Matsuno et al. |
| 2002/0193815 A1 | 12/2002 | Foerster et al. |
| 2003/0028179 A1 | 2/2003 | Piskun |
| 2003/0028207 A1 | 2/2003 | Lang et al. |
| 2003/0073882 A1 | 4/2003 | Smid et al. |
| 2003/0100814 A1 | 5/2003 | Kindlein |
| 2003/0109898 A1 | 6/2003 | Schwarz et al. |
| 2003/0113540 A1 | 6/2003 | Anderson et al. |

(56) References Cited

U.S. PATENT DOCUMENTS

| | | |
|---|---|---|
| 2003/0114838 A1 | 6/2003 | O'Neill et al. |
| 2003/0120285 A1 | 6/2003 | Kortenbach |
| 2003/0135204 A1 | 7/2003 | Lee et al. |
| 2003/0139756 A1 | 7/2003 | Brustad |
| 2003/0206860 A1 | 11/2003 | Bleyer et al. |
| 2003/0208207 A1 | 11/2003 | Layer |
| 2003/0225420 A1 | 12/2003 | Wardle |
| 2003/0229338 A1 | 12/2003 | Irion et al. |
| 2003/0236549 A1 | 12/2003 | Bonadio et al. |
| 2004/0015185 A1 | 1/2004 | Ewers et al. |
| 2004/0023161 A1 | 2/2004 | Yamaguchi et al. |
| 2004/0024304 A1 | 2/2004 | Foerster et al. |
| 2004/0068291 A1 | 4/2004 | Suzuki |
| 2004/0106942 A1 | 6/2004 | Taylor et al. |
| 2004/0106986 A1 | 6/2004 | Andersson et al. |
| 2004/0138525 A1 | 7/2004 | Saadat et al. |
| 2004/0138528 A1 | 7/2004 | Richter et al. |
| 2004/0147933 A1 | 7/2004 | McGovern |
| 2004/0167545 A1 | 8/2004 | Sadler et al. |
| 2004/0193146 A1 | 9/2004 | Lee et al. |
| 2004/0193212 A1 | 9/2004 | Taniguchi et al. |
| 2004/0215063 A1 | 10/2004 | Bonadio et al. |
| 2004/0225323 A1 | 11/2004 | Nagase et al. |
| 2004/0230160 A1 | 11/2004 | Blanco |
| 2004/0230161 A1 | 11/2004 | Zeiner |
| 2004/0243108 A1 | 12/2004 | Suzuki |
| 2004/0254426 A1 | 12/2004 | Wenchell |
| 2004/0260198 A1 | 12/2004 | Rothberg et al. |
| 2004/0260337 A1 | 12/2004 | Freed |
| 2005/0020884 A1 | 1/2005 | Hart et al. |
| 2005/0033312 A1 | 2/2005 | Suzuki |
| 2005/0033342 A1 | 2/2005 | Hart et al. |
| 2005/0033357 A1 | 2/2005 | Braun |
| 2005/0049580 A1 | 3/2005 | Brock et al. |
| 2005/0085842 A1 | 4/2005 | Eversull et al. |
| 2005/0090809 A1 | 4/2005 | Cooper et al. |
| 2005/0107809 A1 | 5/2005 | Litscher et al. |
| 2005/0124912 A1 | 6/2005 | Griego et al. |
| 2005/0137609 A1 | 6/2005 | Guiraudon |
| 2005/0148823 A1 | 7/2005 | Vaugh et al. |
| 2005/0155611 A1 | 7/2005 | Vaugh et al. |
| 2005/0192483 A1 | 9/2005 | Bonadio et al. |
| 2005/0209608 A1 | 9/2005 | O'Heeron |
| 2005/0222582 A1 | 10/2005 | Wenchell |
| 2005/0228224 A1 | 10/2005 | Okada et al. |
| 2005/0267419 A1 | 12/2005 | Smith |
| 2005/0273084 A1 | 12/2005 | Hinman et al. |
| 2005/0273132 A1 | 12/2005 | Shluzas et al. |
| 2005/0277946 A1 | 12/2005 | Greenhalgh |
| 2006/0016853 A1 | 1/2006 | Racenet |
| 2006/0020241 A1 | 1/2006 | Piskun et al. |
| 2006/0020281 A1 | 1/2006 | Smith |
| 2006/0020287 A1 | 1/2006 | Lee et al. |
| 2006/0042636 A1 | 3/2006 | Nalagatla et al. |
| 2006/0071432 A1 | 4/2006 | Staudner |
| 2006/0094933 A1 | 5/2006 | Goldfarb et al. |
| 2006/0149137 A1 | 7/2006 | Pingleton et al. |
| 2006/0206145 A1 | 9/2006 | Griego et al. |
| 2006/0212062 A1 | 9/2006 | Farascioni |
| 2006/0224129 A1 | 10/2006 | Beasley et al. |
| 2006/0224164 A1 | 10/2006 | Hart et al. |
| 2006/0229501 A1 | 10/2006 | Jensen et al. |
| 2006/0229641 A1 | 10/2006 | Gupta et al. |
| 2006/0229665 A1 | 10/2006 | Wales et al. |
| 2006/0241651 A1 | 10/2006 | Wilk |
| 2006/0241671 A1 | 10/2006 | Greenhalgh |
| 2006/0247499 A1 | 11/2006 | Butler et al. |
| 2006/0247500 A1 | 11/2006 | Voegele et al. |
| 2006/0247516 A1 | 11/2006 | Hess et al. |
| 2006/0247586 A1 | 11/2006 | Voegele et al. |
| 2006/0247673 A1 | 11/2006 | Voegele et al. |
| 2006/0247678 A1 | 11/2006 | Weisenburgh et al. |
| 2006/0258899 A1 | 11/2006 | Gill et al. |
| 2006/0259071 A1 | 11/2006 | Nicholas et al. |
| 2006/0259073 A1 | 11/2006 | Miyamoto et al. |
| 2006/0264706 A1 | 11/2006 | Piskun |
| 2006/0270911 A1 | 11/2006 | Voegele et al. |
| 2007/0027468 A1 | 2/2007 | Wales et al. |
| 2007/0049966 A1 | 3/2007 | Bonadio et al. |
| 2007/0060939 A1 | 3/2007 | Lancial et al. |
| 2007/0085232 A1 | 4/2007 | Brustad et al. |
| 2007/0088202 A1 | 4/2007 | Albrecht et al. |
| 2007/0088277 A1 | 4/2007 | McGinley et al. |
| 2007/0106317 A1 | 5/2007 | Shelton et al. |
| 2007/0118021 A1 | 5/2007 | Pokorney |
| 2007/0151566 A1 | 7/2007 | Kahle et al. |
| 2007/0156119 A1 | 7/2007 | Wallace et al. |
| 2007/0162072 A1 | 7/2007 | Nicholas et al. |
| 2007/0179525 A1 | 8/2007 | Frecker et al. |
| 2007/0185453 A1 | 8/2007 | Michael et al. |
| 2007/0203812 A1 | 9/2007 | Norton et al. |
| 2007/0244358 A1 | 10/2007 | Lee |
| 2007/0250113 A1 | 10/2007 | Hegeman et al. |
| 2007/0255219 A1 | 11/2007 | Vaugh et al. |
| 2007/0260114 A1 | 11/2007 | Miyamoto et al. |
| 2008/0027476 A1 | 1/2008 | Piskun |
| 2008/0039892 A1 | 2/2008 | Mitsuishi et al. |
| 2008/0045803 A1* | 2/2008 | Williams ........... A61B 1/00052 600/204 |
| 2008/0051631 A1 | 2/2008 | Dejima et al. |
| 2008/0051739 A1 | 2/2008 | McFarlane |
| 2008/0064921 A1 | 3/2008 | Larkin et al. |
| 2008/0065021 A1 | 3/2008 | Jenkins et al. |
| 2008/0065107 A1 | 3/2008 | Larkin et al. |
| 2008/0105730 A1 | 5/2008 | Racenet et al. |
| 2008/0119821 A1 | 5/2008 | Agnihotri et al. |
| 2008/0147113 A1 | 6/2008 | Nobis et al. |
| 2008/0154299 A1 | 6/2008 | Livneh |
| 2008/0177134 A1 | 7/2008 | Miyamoto et al. |
| 2008/0183044 A1 | 7/2008 | Colleran et al. |
| 2008/0188891 A1 | 8/2008 | Frank et al. |
| 2008/0255420 A1 | 10/2008 | Lee et al. |
| 2008/0255519 A1 | 10/2008 | Piskun et al. |
| 2008/0255608 A1 | 10/2008 | Hinman et al. |
| 2008/0262492 A1 | 10/2008 | Lee |
| 2008/0269727 A1 | 10/2008 | Lee |
| 2008/0294154 A1 | 11/2008 | Ibrahim et al. |
| 2008/0294191 A1 | 11/2008 | Lee |
| 2009/0005799 A1 | 1/2009 | Franer et al. |
| 2009/0062618 A1 | 3/2009 | Drew et al. |
| 2009/0084826 A1 | 4/2009 | Shah et al. |
| 2009/0088792 A1 | 4/2009 | Hoell, Jr. et al. |
| 2009/0112230 A1 | 4/2009 | Jinno |
| 2009/0171147 A1 | 7/2009 | Lee et al. |
| 2009/0206129 A1 | 8/2009 | Doll et al. |
| 2009/0306658 A1 | 12/2009 | Nobis et al. |
| 2009/0326325 A1 | 12/2009 | Naito et al. |
| 2010/0057121 A1 | 3/2010 | Piskun et al. |
| 2010/0081863 A1 | 4/2010 | Hess et al. |
| 2010/0081864 A1 | 4/2010 | Hess et al. |
| 2010/0081880 A1 | 4/2010 | Widenhouse et al. |
| 2010/0081881 A1 | 4/2010 | Murray et al. |
| 2010/0081882 A1 | 4/2010 | Hess et al. |
| 2010/0081883 A1 | 4/2010 | Murray et al. |
| 2010/0081995 A1 | 4/2010 | Widenhouse et al. |
| 2010/0094289 A1 | 4/2010 | Taylor et al. |
| 2010/0130817 A1 | 5/2010 | Conlon |
| 2010/0179540 A1 | 7/2010 | Marczyk et al. |
| 2010/0228090 A1 | 9/2010 | Weisenburgh, II et al. |
| 2010/0228091 A1 | 9/2010 | Widenhouse et al. |
| 2010/0228092 A1 | 9/2010 | Ortiz et al. |
| 2010/0228094 A1 | 9/2010 | Ortiz et al. |
| 2010/0228096 A1 | 9/2010 | Weisenburgh, II et al. |
| 2010/0228198 A1 | 9/2010 | Widenhouse et al. |
| 2010/0261975 A1 | 10/2010 | Huey et al. |
| 2010/0312060 A1 | 12/2010 | Widenhouse et al. |
| 2010/0312061 A1 | 12/2010 | Hess et al. |
| 2010/0312064 A1 | 12/2010 | Weisenburgh, II et al. |
| 2010/0312065 A1 | 12/2010 | Shelton, IV et al. |
| 2010/0331857 A1 | 12/2010 | Doyle et al. |
| 2011/0027269 A1 | 2/2011 | Marrotta et al. |
| 2011/0028793 A1 | 2/2011 | Martin et al. |
| 2011/0028794 A1 | 2/2011 | Widenhouse et al. |
| 2011/0087236 A1 | 4/2011 | Stokes et al. |

(56) References Cited

U.S. PATENT DOCUMENTS

| | | |
|---|---|---|
| 2011/0087269 A1 | 4/2011 | Stokes et al. |
| 2011/0230875 A1 | 9/2011 | Walberg et al. |
| 2011/0275901 A1 | 11/2011 | Shelton, IV |
| 2011/0276057 A1 | 11/2011 | Conlon et al. |
| 2011/0276083 A1 | 11/2011 | Shelton, IV et al. |
| 2011/0276084 A1 | 11/2011 | Shelton, IV |
| 2012/0024099 A1 | 2/2012 | Main |
| 2012/0078243 A1 | 3/2012 | Worrell et al. |
| 2014/0039518 A1 | 2/2014 | Conlon et al. |
| 2015/0119918 A1 | 4/2015 | Blase et al. |

FOREIGN PATENT DOCUMENTS

| | | |
|---|---|---|
| DE | 9419138 U1 | 3/1995 |
| DE | 19520717 A1 | 12/1996 |
| DE | 202007003093 U1 | 7/2007 |
| EP | 0568383 A1 | 11/1993 |
| EP | 0621009 A1 | 10/1994 |
| EP | 0646358 A1 | 4/1995 |
| EP | 0776231 A1 | 6/1997 |
| EP | 0950376 A1 | 10/1999 |
| EP | 0966924 A1 | 12/1999 |
| EP | 0996925 A1 | 5/2000 |
| EP | 1219251 A1 | 7/2002 |
| EP | 1219252 A1 | 7/2002 |
| EP | 1219253 A1 | 7/2002 |
| EP | 1350476 A1 | 10/2003 |
| EP | 1621139 A2 | 2/2006 |
| EP | 1731105 A1 | 12/2006 |
| FR | 2710270 A1 | 3/1995 |
| JP | 2000033089 A | 2/2000 |
| JP | 2006320750 A | 11/2006 |
| WO | WO-94/26175 A1 | 11/1994 |
| WO | WO-96/08208 A1 | 3/1996 |
| WO | WO-96/008897 A1 | 3/1996 |
| WO | WO-97/12557 A1 | 4/1997 |
| WO | WO-97/29709 A1 | 8/1997 |
| WO | WO-97/35521 A1 | 10/1997 |
| WO | WO-98/10712 A1 | 3/1998 |
| WO | WO-99/03536 A1 | 1/1999 |
| WO | WO-00/30592 A1 | 6/2000 |
| WO | WO-00/32253 A1 | 6/2000 |
| WO | WO-02/17810 A2 | 3/2002 |
| WO | WO-02/39890 A2 | 5/2002 |
| WO | WO-02/39918 A1 | 5/2002 |
| WO | WO-02/058543 A2 | 8/2002 |
| WO | WO-02/094133 A1 | 11/2002 |
| WO | WO-03/005890 A2 | 1/2003 |
| WO | WO-03/067341 A2 | 8/2003 |
| WO | WO-03/077730 A2 | 9/2003 |
| WO | WO-03/091839 A2 | 11/2003 |
| WO | WO-2005/087112 A1 | 9/2005 |
| WO | WO-2005/094432 A2 | 10/2005 |
| WO | WO-2006/110733 A2 | 10/2006 |
| WO | WO-2007/119232 A2 | 10/2007 |
| WO | WO-2008/012787 A2 | 1/2008 |
| WO | WO-2008/024502 A2 | 2/2008 |
| WO | WO-2009/073577 A2 | 6/2009 |
| WO | WO-2010/030114 A2 | 3/2010 |

OTHER PUBLICATIONS

"Adult Cardiac Surgical Instruments," from the website of Genesee BioMedical, Inc. (date of first publication unknown; downloaded May 3, 2007; 4 pages).
"Applied GelPort Advanced Access Device," by Applied Medical Resources Corporation (Nov. 2002).
"Applied GelPort System" by Applied Medical Resources Corporation (2004).
"Bard® Bi-Directional and Kelly-Wick Tunnelers—Instructions for Use," by Bard Peripheral Vascular (Apr. 2006).
"Hand Instruments," from the website of Olympus Surgical America (date of first publication unknown; downloaded May 3, 2007; 4 pages).
"intrack XT—Low Profile Atraumatic Clamps," by Novare Surgical Systems, Inc. (2002).
"Pen Competitors," (date of first publication unknown but no later than May 15, 2007, date of citation in U.S. Appl. No. 11/398,985; 1 page).
Advanced Surgical Concepts (ASC), 510(k) TriPort Laparoscopic Access Device, Dec. 26, 2007, 8 pages.
Ashida, R. et al., "Indocyanine Green is an Ideal Dye for Endoscopic Ultrasound-Guided Fine-Needle Tattooing of Pancreatic Tumors" *Endoscopy*, 38, pp. 190-192 (2006).
Desai, M. et al., "Laprascopic and Robtoic Urology: Scarless single port transumbilical nephrectomy and pyeloplasty: first clinical report," Journal Compilation, 2008 BJU International, 101, 83-88.
http://www.innomedic.de/en/products/innomotion_overview.php (Innomedic Products), accessed Oct. 24, 2006.
http://www.intuitivesurgical.com/products/index.aspx (Intuitive Surgical Products), accessed Oct. 24, 2006.
http://www.lap-laser.com/e/laser_m/prod/med.html (LAP Laser Application), accessed Oct. 24, 2006.
Ideas for Surgery.com, "Surgeon performs single-port laparoscopic surgery," dated Dec. 1, 2007.
International Preliminary Report on Patentability for Application No. PCT/US2011/035525, dated Nov. 13, 2012. (7 pages).
International Preliminary Report on Patentability for Application No. PCT/US2011/035526, dated Nov. 13, 2012. (7 pages).
International Search Report and Written Opinion for Application No. PCT/US2011/035525, dated Aug. 19, 2011. (12 pages).
International Search Report and Written Opinion for Application No. PCT/US2011/035526, dated Aug. 19, 2011. (12 pages).
International Search Report for PCT/US2011/035511 dated Oct. 10, 2011.
Lee, D.I. et al., "Novel Approach to Minimizing Trocar Sites during Challenging Hand-Assisted Laparoscopic Surgery Utilizing the Gelport: Trans-Gel Instrument Insertion and Utilization," *Journal of Endourology*, vol. 17, No. 2, pp. 69-71 (Mar. 2003).
Maurin, et al., "A new robotic system for CT-guided percutaneous procedures with haptic feedback," LSIIT (UMR CNRS-ULP 7005), Louis Pasteur University, Bd. S. Brant, BP 10413, Strasbourg Illkirch 67412, France.
Maurin, et al., "A Parallel 5 DOF Positioner for Semi-Spherical Workspaces", Proceedings of DETC'04, ASME 2004 Design Engineering Technical Conferences and Computers and Information in Engineering Conference, Sep. 28-Oct. 2, 2004, Salt Lake City Utah USA.
Maurin, et al., "A Parallel Robotic System with Force Sensors for Percutaneous Procedures Under CT-Guidance", LSIIT (UMR CNRS-ULP 7005), Strasbourg I University Bd. S. Brant, BP 10413, 67412 Illkirch cedex, France.
Stoianovici, et al., "A Novel Mechanical Transmission Applied to Percutaneous Renal Access", DSC-vol. 61, Proceedings of the ASME Dynamic Systems and Control Division 1997.
Twentieth Edition—Illustrations of Surgical Instruments, by the Kny-Scheerer Company, New York, USA, pp. 1003, 1026, 1028-1029, 1133, 2034, 2068-2069, 2097-2099, 2132, 2137, 2144, 2155-2156, 2162, 2167-2171, 2173, 2175, 2244, 2255, 2281-2282, 2327, 2333, 2338-2348, 2352, 2355, 2359, 2371, 3017, 3039-3073, 3132, 3165, 3168-3169, 3208-3209, 3219 (Jul. 1915).
URobitics, Brady Urological Institute, Johns Hopkins Medical Institutions, "Z-Stage PAKY", date of publication unknown but no later than Oct. 26, 2006 (date of citation in U.S. Appl. No. 11/307,231).
URobotics, Brady Urological Institute, Johns Hopkins Medical Institutions, "PAKY Needle Driver," date of publication unknown but no later than Oct. 26, 2006 (date of citation in U.S. Appl. No. 11/307,231).
URobotics, Brady Urological Institute, Johns Hopkins Medical Institutions, "The RCM Robot", date of publication unknown but no later than Oct. 26, 2006 (date of citation in U.S. Appl. No. 11/307,231).
Webpage of Novare Surgical, Inc. featuring clamps (date of first publication unknown; downloaded Feb. 23, 2004; 1 page).

(56) References Cited

OTHER PUBLICATIONS

Written Opinion issued in International Application No. PCT/US2011/035526 dated Aug. 19, 2011.

* cited by examiner

COMPOUND ANGLE LAPAROSCOPIC METHODS AND DEVICES

CROSS REFERENCE TO RELATED APPLICATIONS

The present application is a continuation of U.S. application Ser. No. 14/032,747, filed Sep. 20, 2013, and entitled "Compound Angle Laparoscopic Methods and Devices," which is a continuation of U.S. application Ser. No. 12/775,724, filed May 7, 2010 (now U.S. Pat. No. 8,562,592) and entitled "Compound Angle Laparoscopic Methods and Devices," which are hereby incorporated by reference in their entireties.

FIELD OF THE INVENTION

The present invention relates to methods and devices for performing minimally invasive surgical procedures.

BACKGROUND OF THE INVENTION

Many surgical procedures involve inserting various instruments through the working channel of a surgical access device. The instruments are used to view, engage, and/or treat tissue within a body cavity or other surgical site to achieve a diagnostic or therapeutic effect. In laparoscopic abdominal procedures for example, the abdominal cavity is generally insufflated with $CO_2$ gas to a pressure of around 15 mm Hg. The abdominal wall is pierced and a plurality of tubular cannulas, each defining a working channel, are inserted at various points into the abdominal cavity. A laparoscopic telescope connected to an operating room monitor can be used to visualize the operative field and can be placed through one of the cannulas. Other laparoscopic instruments such as graspers, dissectors, scissors, retractors, etc. can be placed through the other cannula(s) to facilitate various manipulations by the surgeon. In this type of procedure, because of the positioning of the cannulas, it can be relatively easy to "triangulate" the tips of two separate instruments, e.g., bring the tips together at a single point within the abdominal cavity. For example, a first instrument could be passed through a cannula in the left side of the patient's abdomen and operated with the surgeon's left hand while a second instrument could be passed through another cannula in the right side of the patient's abdomen and operated with the surgeon's right hand. The surgeon can then easily bring the tips of the two instruments together at an internal point, e.g. in the center of the patient's abdomen. A laparoscope viewing instrument can also be passed through a third cannula, positioned for example in the center of the patient's abdomen, such that the tips of the two instruments can be easily visualized from above.

In other surgical procedures, however, visualization and triangulation is not as straightforward. For example, in Single Incision Laparoscopic Surgery (SILS) or Single Site Laparoscopic Surgery (SSLS), a single laparoscopic entry point is formed, e.g., through the navel. An access device having one or more working channels, and typically a plurality of working channels, is then installed in the entry point and all instruments required for performing the surgery are inserted through this same access device. In such procedures, the elongate shafts of the various instruments end up being generally parallel to one another while inserted through the access device. This can make it very difficult to triangulate the tips of two instruments within the abdominal cavity, especially if the instruments do not have distal articulation capabilities. In addition, since the viewing scope is inserted generally along the same axis as the various other instruments, it can be difficult or impossible to see the tips of the instruments. Furthermore, the handles of the various instruments often end up being positioned in close proximity to one another and create a so-called "chopstick" effect, which describes interference between the surgeon's hands, between the surgeon's hands and the instruments, and between the instruments. Interference between the handles and/or the positioning of the handles can limit maneuverability and/or lead to discomfort for the surgeon. These problems can unduly lengthen the duration of the surgery, potentially increasing the risk of patient complications. Also, in cases where it is impossible to achieve adequate triangulation and/or visualization, a second or even third entry point must be formed, increasing trauma to the patient and creating additional scars.

Even in multiple-incision procedures or where triangulation and visualization is possible (e.g., where one or more of the devices includes a distal articulation capability), triangulation, visualization, comfort, and maneuverability can still be sub-optimal.

Accordingly, there is a need for methods and devices which allow laparoscopic procedures to be performed with an enhanced ability to triangulate and visualize surgical instruments and with improved surgeon comfort and instrument maneuverability.

SUMMARY OF THE INVENTION

The present invention generally provides methods and devices for performing minimally invasive surgical procedures. In one embodiment, an articulating laparoscopic access device is provided that includes an elongate shaft, first and second linkages, and a linkage bar. The first and second linkages and the linkage bar each have proximal and distal ends. The proximal end of the first linkage is pivotally coupled to the distal end of the elongate shaft at a first pivot point. The proximal end of the linkage bar is pivotally coupled to the distal end of the first linkage by a second pivot point, and the distal end of the linkage bar is pivotally coupled to the proximal end of the second linkage by a third pivot point. A first range of motion of the linkage bar about the third pivot point is less than a second range of motion of the linkage bar about the second pivot point. The distal end of the first linkage, the proximal end of the second linkage, and the linkage bar are movable between a first position longitudinally aligned with a longitudinal axis of the elongate shaft and a second position displaced from the longitudinal axis of the elongate shaft.

The device can include an actuator. The distal end of the second linkage can be pivotally coupled to the actuator at a fourth pivot point. The actuator can be movable longitudinally relative to the elongate shaft to longitudinally move the distal end of the second linkage.

The linkages and the linkage bar can have a variety of configurations and be coupled together in a variety of ways. For example, the proximal end of the linkage bar can be seated within a first groove formed in the distal end of the first linkage, and the distal end of the linkage bar can be seated within a second groove formed in the proximal end of the second linkage. The first groove can define the first range of motion, and the second groove can define the second range of motion. For another example, the elongate shaft, the first linkage, and the second linkage can have an inner lumen extending longitudinally therethrough for receiving a tool.

An end effector can be coupled to the distal end of the second linkage. The end effector can have a variety of configurations, but in one embodiment, it can include opposed jaws. The device can include an actuator configured to move the opposed jaws between a closed position and an open position. The actuator can extend through the elongate shaft, the first linkage, and the second linkage and be coupled to a proximal end of the opposed jaws.

In another aspect, a laparoscopic system is provided that includes an articulation device and a tool. The articulation device has an elongate shaft, a first linkage coupled to the elongate shaft at a first joint, and a second linkage coupled to the first linkage at a second joint. The second joint is movable radially outward relative to an axis extending longitudinally along the elongate shaft, and a distal end of the second linkage is constrained to longitudinal movement along the axis. The tool has a flexible elongate shaft with an end effector on a distal end thereof. The flexible elongate shaft is disposable through a lumen extending through the elongate shaft, the first linkage, and the second linkage such that the end effector extends from the distal end of the second linkage. The flexible elongate shaft is bendable to conform to a shape of the lumen as the second joint is moved radially outward.

The system can include an actuator extending along the elongate shaft and having a distal end coupled to the distal end of the second linkage. The actuator can be longitudinally movable relative to the axis to move the distal end of the second linkage along the axis. The distal end of the actuator can be coupled to the distal end of the second linkage at a pivot point such that the second linkage is configured to pivot about the pivot point relative to the actuator. In some embodiments, the actuator is rigid. The system can optionally include a lock configured to lock the actuator in a fixed position relative to the shaft and the first and second linkages.

The first and second joints can be configured in any number of ways. For example, the first joint can include a pivot point formed between a distal end of the elongate shaft and a proximal end of the first linkage, and/or the second joint can include a linkage bar having a proximal end pivotally coupled to a distal end of the first linkage at a first pivot point and a distal end pivotally coupled to a proximal end of the second linkage at a second pivot point. For another example, the end effector can be angularly oriented relative to the axis when the second joint is disposed radially outward from the axis.

In yet another aspect, a method for laparoscopic surgery is provided that includes inserting a first tool through a first port formed in a housing disposed within tissue to position a distal end of the first tool within a body cavity, inserting a second tool through a second port formed in the housing to position a distal end of the second tool within the body cavity, inserting a flexible elongate shaft through a lumen of one of the first and second tools, actuating the first tool to cause a distal portion of the first tool disposed within the body cavity to form a compound angle, and actuating the second tool to cause a distal portion of the second tool disposed within the body cavity to form a compound angle. The flexible elongate shaft bends to conform to a shape of the lumen with the distal portion of the one of the first and second tools. When proximal portions of each of the first and second tools are substantially parallel, actuating the first and second tools causes end effectors at the distal ends of the first and second tools to be oriented toward one another without causing the distal portions of the first and second tools to intersect. In some embodiments, actuating the first tool can include longitudinally moving a first actuator extending along a first elongate shaft of the first tool, and actuating the second tool can include longitudinally moving a second actuator extending along a second elongate shaft. The method can optionally include engaging a lock of at least one of the first and second tools to maintain the compound angle of the one of the first and second tools in a fixed position.

The end effector can have a variety of configurations. In some embodiments, the method can include actuating the first tool to move opposed jaws of the end effector of the first tool between a closed position and an open position, wherein the formed compound angle of the first tool remains fixed during actuation of the first tool.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
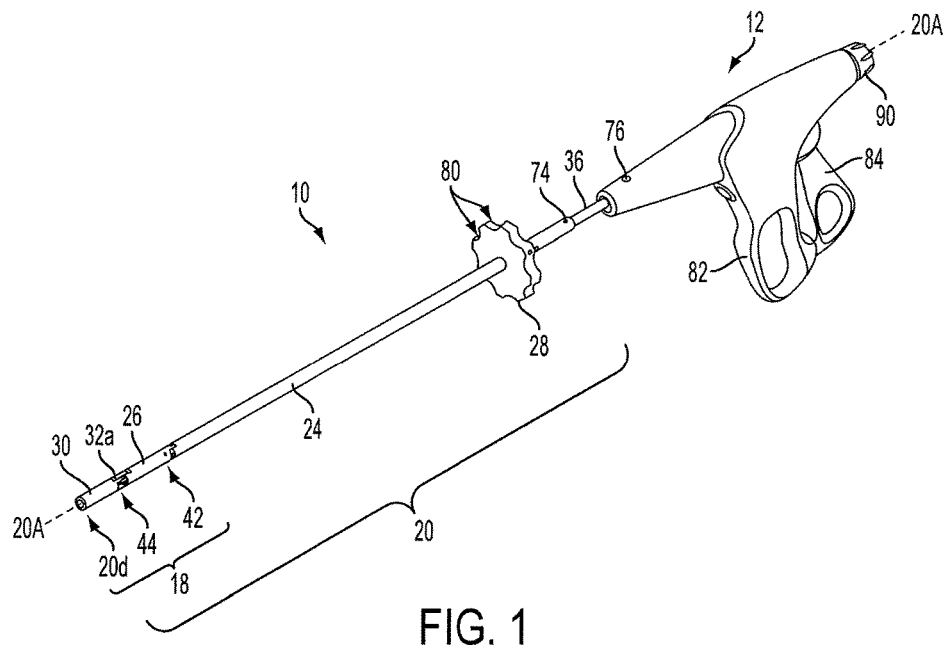
FIG. 1 is a perspective view of one embodiment of a laparoscopic device including a handle and an articulatable shaft extending distally from the handle, the shaft being in a straight configuration.
Figure 2A:
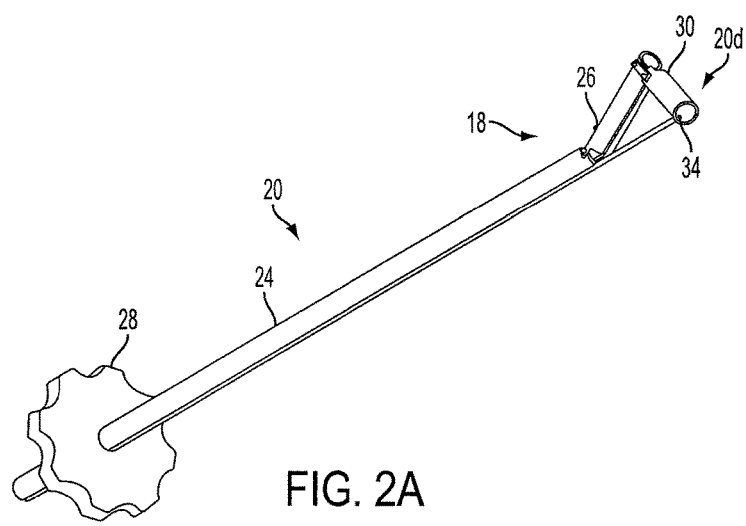
FIG. 2A is a perspective view of the articulatable shaft of FIG. 1 showing the shaft in an articulated configuration.
Figure 2B:
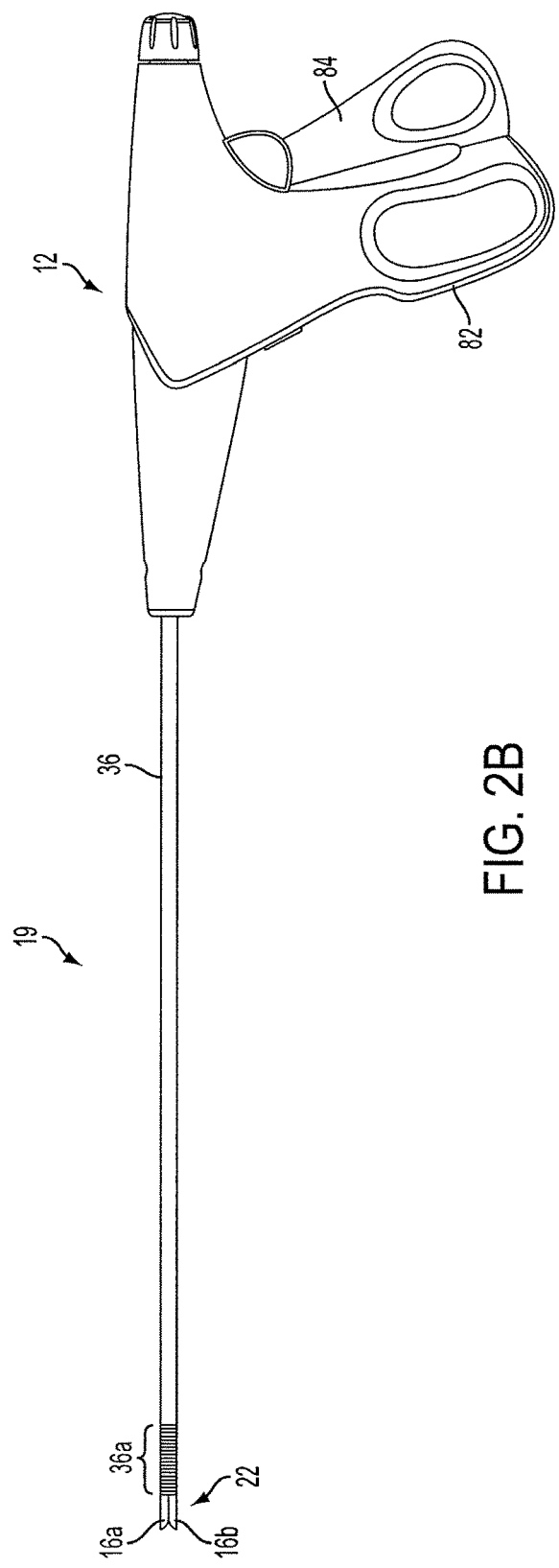
FIG. 2B is a perspective view of the device of FIG. 1 showing an inner shaft having an end effector coupled to a distal end thereof with the articulatable shaft omitted for clarity.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various exemplary devices and methods are provided for performing minimally invasive surgical procedures. In general, the devices and methods allow a shaft of a surgical instrument to form a compound angle, thereby facilitating optimal positioning of a working distal end of the instrument relative to a surgical site. In an exemplary embodiment, a laparoscopic device includes an elongate shaft having a distal portion configured to be movable between a first configuration in which the distal portion of the shaft is substantially straight or linear and a second configuration in which the distal portion of the shaft is bent at a compound angle. In an exemplary embodiment, the shaft's distal portion can include two articulation joints to facilitate formation of the compound angle. The shaft's distal portion can be configured to be articulated in a wide range of compound angles. The shaft's distal portion can also be configured to be locked in a fixed articulated position, thereby allowing the device to be easily held in a desired bent position. The device can thus be inserted into a patient's body with the shaft in the first configuration, and it can be subsequently manipulated to move the shaft from the first configuration to the second configuration to allow the device's working distal end, e.g., an end effector, to be optimally angled within the body relative to a surgical site and/or any other surgical instruments at the surgical site. The shaft can also be configured to move from the second configuration to the first configuration to ease removal of the device from the patient. Such a configuration can be particularly advantageous where two or more instruments are inserted into a patient's body cavity through the same entry port in tissue because it can allow for triangulation. In particular, distal tips of the instruments can be brought together at a single point within the body cavity, even though the instruments' shafts extend generally parallel to one another.

A person skilled in the art will appreciate that while the methods and devices are described in connection with laparoscopic procedures in which one or more surgical instruments are inserted into a patient's body through an artificial opening, e.g., an incision, the methods and devices disclosed herein can be used in numerous surgical procedures and with numerous surgical instruments. By way of non-limiting example, the methods and devices can be used in open surgical procedures.

A person skilled in the art will also appreciate that the devices disclosed herein can be inserted into a body in any way, such as through a natural orifice, through an incision or puncture hole formed in tissue, etc. The devices can be inserted directly into a patient's body or can be inserted through an access device having a working channel through which a shaft of a surgical instrument can be advanced. A person skilled in the art will further appreciate that an access device can be configured to allow insertion of a single surgical instrument therethrough, such as with a straight cannula, or to allow simultaneous insertion of multiple instruments therethrough, such as with a surgical access device having multiple sealing ports each defining a working channel. Devices disclosed herein can alternatively or additionally be introduced into a body through an auxiliary passageway along the outside of a scoping device or other surgical instrument, as will be appreciated by a person skilled in the art. Exemplary embodiments of a surgical instrument that provides such an auxiliary passageway are described in more detail in U.S. Pat. No. 7,615,005 issued Nov. 10, 2009 entitled "Medical Apparatus For Use With An Endoscope," which is hereby incorporated by reference in its entirety.

In an exemplary embodiment, shown in FIGS. 1-4, a surgical device 10 is provided that includes a proximal handle 12 having a shaft assembly 20 surrounding an elongate shaft 36 extending distally therefrom. The shaft 36 can have a working element or end effector 22, generally referred to as an "end effector," at a distal end thereof. As shown in FIGS. 2A and 2B, the device 10 in the illustrated embodiment includes the shaft assembly 20 and a tool 19 including the shaft 36 releasably receivable within the shaft assembly 20 such that the end effector 22 at a distal end of the shaft 36 can extend distally beyond a distal end 20d of the shaft assembly 20. As discussed further below, articulation of the shaft assembly 20 can articulate a distal portion 36a of the shaft 36. Although the shaft assembly 20 and the tool 19 can be separate units as in the illustrated embodiment, the shaft assembly 20 and the tool 19 can be integrally formed, as also discussed further below. The end effector 22 is omitted from FIGS. 1, 3, and 4 for clarity. The end effector 22 in the illustrated embodiment includes a tissue grasper having a pair of opposed jaws 16a, 16b configured to move between open and closed positions, but as will be appreciated by a person skilled in the art the end effector 22 can include any tool, e.g., a grasper, a dissector, scissors, forceps, a retractor, a light, etc. As discussed further below, the handle 12 can be configured to operate the end effector 22, and a control knob 28 at a location distal of the handle 12 can be configured to facilitate articulation and/or rotation of at least a portion of the shaft assembly 20.

The shaft assembly 20 can have a variety of sizes, shapes, and configurations. The shaft assembly 20 can be rigid, flexible, or a combination thereof. Portions of the shaft assembly 20 can be less flexible or more rigid than a remainder of the shaft assembly 20 to facilitate insertion through tissue and/or operation of the end effector 22. As in the illustrated embodiment, the distal portion 36a of the shaft 36 can be flexible, and a remainder of the tool 19, as well as the shaft assembly 20, can be rigid. Having a rigid shaft assembly 20 and a shaft 36 rigid along a substantial longitudinal length thereof can help facilitate translation of forces in articulating and actuating the device 10 as discussed further below.

Figure 4:
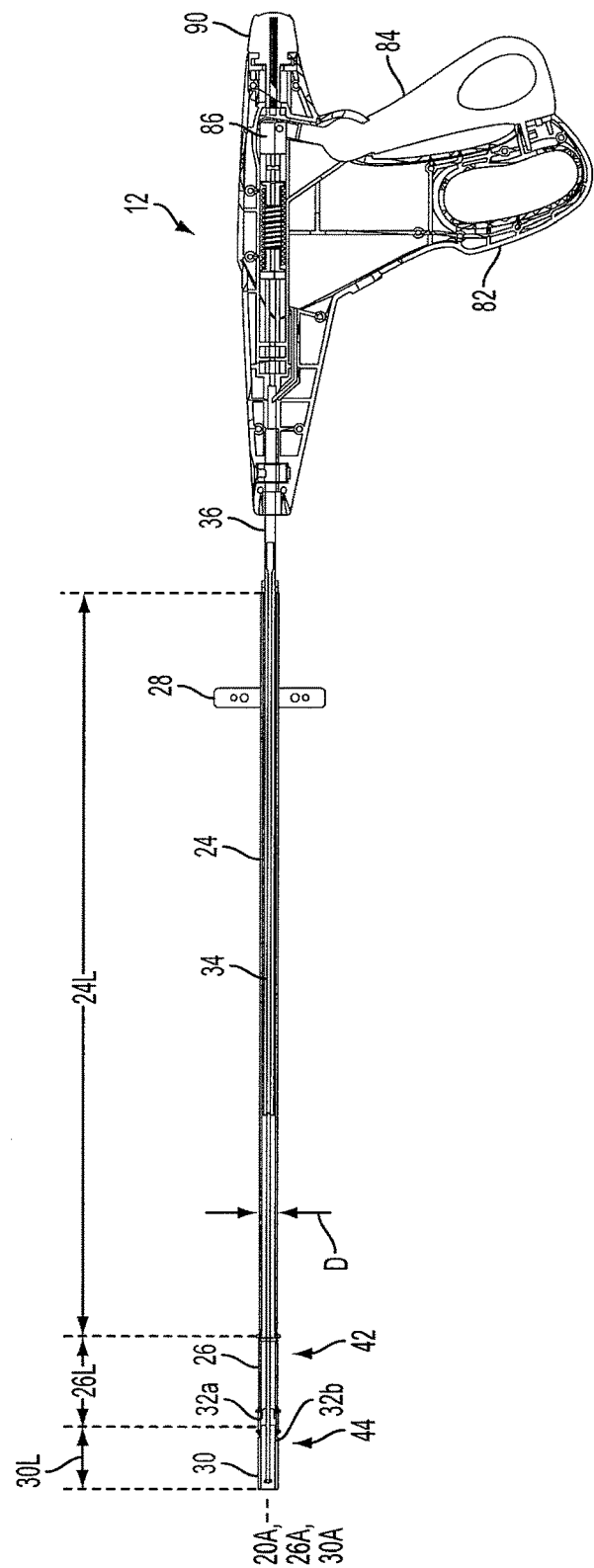
FIG. 4 is a cross-sectional side view of the device of FIG. 3.

As mentioned above, the shaft assembly 20 can be tubular, and it can have an inner lumen 34 extending therethrough, as shown in FIG. 4, which can receive the shaft 36. A person skilled in the art will also appreciate that although the inner lumen 34 in the illustrated embodiment extends along a longitudinal axis of the shaft assembly 20 through the shaft assembly 20 and the handle 12, the inner lumen 34 can be at least partially radially/laterally offset from the shaft's longitudinal axis 20A, extend through the shaft assembly 20 and only a portion of the handle 12, and/or extend only through a portion of the shaft assembly 20. The device's inner lumen 34 can be configured to slidably receive the shaft 36 such that when the shaft 25 extends through the device's articulation assembly 18, articulation of the articulation assembly 18 can correspondingly articulate the shaft 36 at the flexible portion 36a thereof in a compound angle and thus facilitate optimal positioning of the end effector 22. The tool's handle and/or a portion of the tool's shaft 36 can be configured to lock to shaft assembly 20, e.g., with a J-lock, spring-loaded detent, etc., to help prevent unintentional movement of the end effector 22 when it is optimally positioned relative to the device's shaft assembly 20.

The shaft assembly 20 can have any longitudinal length, although in an exemplary embodiment it is long enough to allow the handle 12 and the control knob 28 to be manipulated outside a patient's body when the device 10 is partially inserted into the body with the end effector 22 disposed within a body cavity, e.g., have a longitudinal length of about 33 cm. In this way, the shaft assembly 20 and the end effector 22 can be easily manipulated when the device 10 is in use during a surgical procedure. The shaft assembly 20 can have any diameter D, e.g., less than or equal to about 10 mm, and more particularly less than or equal to about 5 mm, to allow for insertion of the shaft assembly 20 through an access device, such as during a laparoscopic surgical procedure. The end effector 22 coupled to the shaft's distal end can have a diameter equal to or less than the shaft's diameter D, at least when the jaws 16a, 16b are in a closed position, to further facilitate insertion of the device's distal portion into a patient's body.

Figure 3:
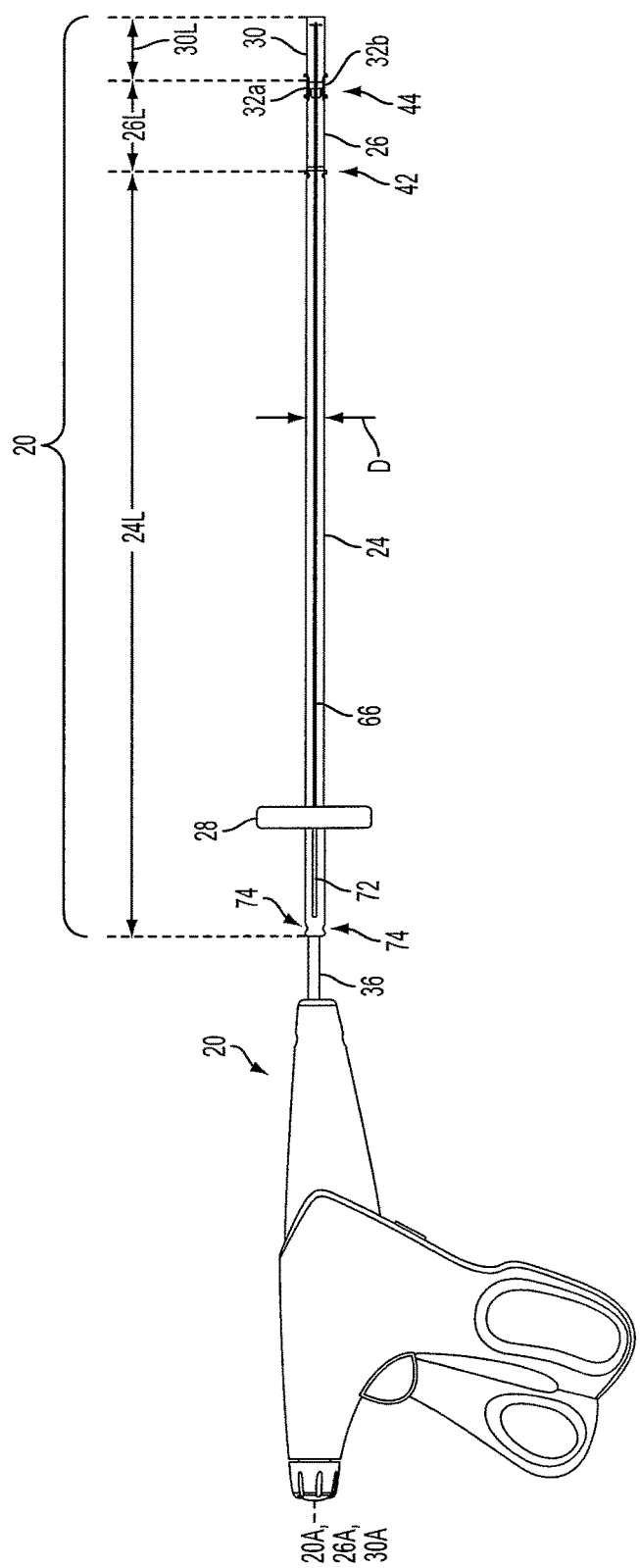
FIG. 3 is a side view of the device of FIG. 1.

In an exemplary embodiment, the shaft assembly 20 can be substantially cylindrical to help the shaft assembly 20 pass smoothly into a body. The shaft assembly 20 can have any constant or varying shape along its longitudinal length, and the shaft's diameter D can be uniform or non-uniform along its longitudinal length. In an exemplary embodiment, as shown in FIGS. 3 and 4, the shaft assembly 20 can have a substantially uniform diameter D along its longitudinal length except at one or both of the articulation joints 42, 44, which can have diameters that differ from the shaft's diameter D, as discussed further below.

Generally, the shaft assembly 20 can include an articulation assembly 18 surrounding at least the distal portion 36a of the shaft 36 when the shaft 36 is received within the shaft assembly 20. The articulation assembly 18 can be movable relative to the shaft 36 to articulate the distal portion of the shaft assembly 20 and the distal portion 36a of the shaft 36 received therein and generally aligned with the articulation assembly 18. Generally, the articulation assembly 18 can be configured to be movable between a linear or straight configuration, generally referred to as a "straight configuration," in which the articulation assembly 18 extends substantially parallel to a longitudinal axis 20A of the shaft assembly 20, as illustrated in FIGS. 2-4, and an articulated, bent, or compound angle configuration, generally referred to as an "articulated configuration," in which portions of the articulation assembly 18 do not extend parallel to the longitudinal axis 20A, as illustrated in FIG. 1. In the illustrated exemplary embodiment, the articulation assembly 18 is biased to the straight configuration, e.g., in a configuration with the knob 28 slid distally because of a tendency of the shaft's distal portion 36a to return to a straight or linear configuration. As will be appreciated by a person skilled in the art, the articulation assembly 18 can be biased in any other way, e.g., using a shape memory material, it can be unbiased, or it can be biased to the articulated configuration. Although the articulation assembly 18 can be located anywhere along the shaft assembly 20, e.g., positioned at a mid-portion thereof, as shown in the illustrated embodiment, it can be located in a distal portion thereof such that a distal portion of the device 10 can be configured to articulate to form a compound angle. Similarly, the flexible distal portion 36a of the shaft 36 can be located anywhere along the shaft 36, as in the illustrated embodiment, it can be located in a distal portion thereof. Although the shaft assembly 20 can be configured to bend any number of times to form a compound angle, the articulation assembly 18 in the illustrated embodiment is articulated at first and second articulation joints 42, 44 to form a triangulated compound angle, as discussed in further detail below.

The articulation assembly 18 can have a variety of sizes, shapes, and configurations. Generally, it can include a plurality of sections, segments, or linkages, generally referred to as "linkages," along the shaft's longitudinal length to facilitate articulation of the shaft assembly 20. As shown in the embodiment illustrated in FIGS. 1-11, the articulation assembly 18 can include a proximal elongate shaft 24, a first linkage 26 coupled to a distal end of the proximal shaft 24, and a second linkage 30 coupled to a distal end of the first linkage 30. The first and second linkages 26, 30 can be coupled together with at least one bar or rod, generally referred to as a "linkage bar" located between the first and second linkages 26, 30. In the illustrated embodiment, the articulation assembly 18 includes identical first and second linkage bars 32a, 32b on opposite sides of the shaft assembly 20, e.g., separated about 180° from one another around the shaft's circumference. While two shaft linkages are illustrated in the embodiment of FIGS. 1-11, a person skilled in the art will appreciate that in other embodiments, the device can include any number of linkages.

Figure 8:
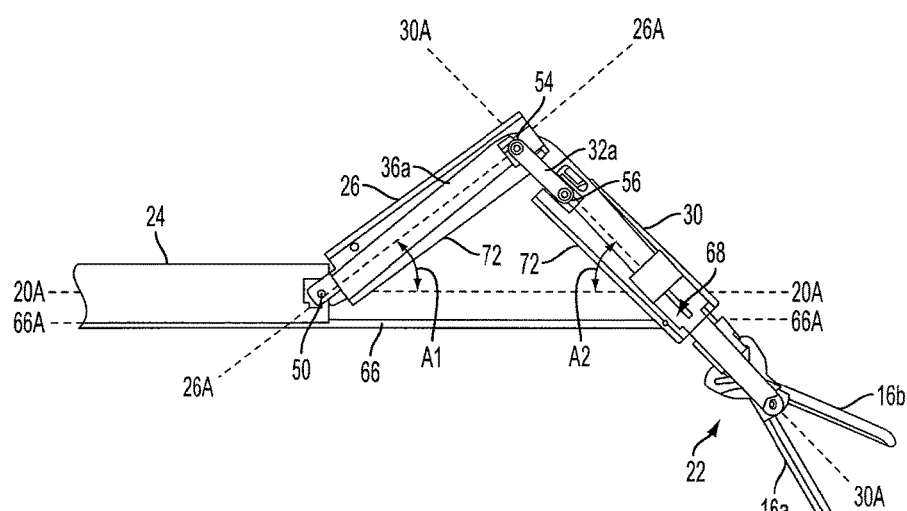
FIG. 8 is a side, partially transparent view of a distal portion of the device of FIG. 1 with the end effector shown.

As shown in FIG. 8, when the articulation assembly 18 is in the articulated configuration, and the tool 19 is inserted therein such that the end effector 22 extends distally beyond the assembly's distal end 20d, the end effector 22 can be configured to be oriented transverse to, and optionally to intersect or "cross," the shaft's longitudinal axis 20A, which can facilitate optimal positioning of the end effector 22 relative to other devices and/or a surgical site, and which can reduce a "chopstick" effect between the device 10 and any other adjacent surgical instruments. Depending on the size of the first and second linkages 26, 30 and on the amount the articulation assembly 18 is articulated, the distal portion of second linkage 30 can also intersect or "cross" the shaft's longitudinal axis 20A.

The proximal shaft 24 and the linkages 26, 30 can have a variety of sizes, shapes, and configurations. For example, the proximal shaft 24 and the linkages 26, 30 can each be in the form of a relatively rigid tubular section, e.g., made from a generally non-bendable material such as a hard polymer or titanium, with the inner lumen 34 extending therethrough. As shown in FIGS. 3 and 4 of the illustrated embodiment, the proximal shaft 24 can have a longer longitudinal length 24L than the first and second linkages 26, 30 alone or together. Also as in the illustrated embodiment, a longitudinal length 26L of the first linkage 26 can be longer than a longitudinal length 30L of the second linkage 30. Alternatively, the longitudinal length 30L of the second linkage 30 can be larger than the longitudinal length 26L of the first linkage 26, or the first and second linkages 26, 30 can have substantially equal longitudinal lengths 26L, 30L.

As shown in FIGS. 2-4, a proximal portion of the shaft 36 can be disposed within the handle 12 with a remainder of the shaft 36 extending distally from the handle 12 in a generally straight line parallel to the shaft's longitudinal axis 20A. The distal portion of the shaft 36 can be at least partially received in the inner lumen 34 and surrounded by the proximal shaft 24, which can be slidable around and relative to the shaft 36 to facilitate articulation at the articulation joints 42, 44, as discussed further below.

The articulation assembly 18 can be configured to facilitate smooth and controlled articulation of the shaft assembly 20 relative to the handle 12 with the first articulation joint 42 being located between the proximal shaft 24 and the first linkage 26 to allow the proximal shaft 24 and the first linkage 26 to be angled relative to one another, and with the second articulation joint 44 being located between the first and second linkages 26, 30 to allow the first and second linkages 26, 30 to be angled relative to one another offset from the shaft's longitudinal axis 20A. The proximal shaft 24 and the linkages 26, 30 can thus be configured to articulate to form a compound angle. The proximal shaft 24 can be configured to be in a fixed position along the shaft's longitudinal axis 20A when the articulation assembly 18 is in the straight configuration, as shown in FIGS. 1 and 3-6, and in the articulated configuration, as shown in FIG. 8. In contrast, the first and second linkages 26, 30 and the linkage bars 32a, 32b can be configured to be longitudinally aligned with the shaft's longitudinal axis 20A when the articulation assembly 28 is in the straight configuration, as shown in FIGS. 1, 3-7, and 9, and the first and second linkages 26, 30 can be angularly oriented relative to the shaft's longitudinal axis 20A with the linkage bars 32a, 32b positioned away from the axis 20A when the articulation assembly 18 is in the articulated configuration, as shown in FIG. 8. As mentioned above, the end effector 22 can be coupled to a distal end of the shaft assembly 20 such that the end effector 22 is positioned distal to the articulation joints 42, 44. This can allow the end effector 22 to articulate with the articulation assembly 18 and thereby be angularly oriented relative to the shaft's longitudinal axis 20A in coordination with the second linkage 30, as illustrated in FIG. 8. In this way, the shaft assembly 20 can be inserted into a patient's body, and the distal portion thereof can be articulated inside the body without altering the angular position of the proximal portion of the shaft assembly 20, e.g., the proximal shaft 24, that extends through an opening in the body, either directly or through an access device. The end effector 22 can thus be oriented to extend toward and in a facing relationship with the longitudinal axis 20A.

With the articulation assembly 18 in the articulated configuration, a compound angle is formed, with the respective axes 20A, 26A, 30A of the proximal shaft 24 and the linkages 26, 30 intersecting one another. The axes 20A, 26A, 30A can, however, all lie within a common plane.

The proximal shaft 24 and the linkages 26, 30 can be coupled together in a variety of ways. As illustrated in the embodiment of FIGS. 5-9, a distal end of the proximal shaft 24 can be pivotably coupled to a proximal end of the first linkage 26 at a first pivot point 38 to form the first articulation joint 42. The first linkage 26 can thereby be configured to pivot or rotate, as shown in FIG. 8, relative to the proximal shaft 24 and the handle 12 about the first pivot point 38, which can have an axis that is generally perpendicular to the longitudinal axis 20A of the proximal shaft 24. The proximal end of the first linkage 26 can thus be in a fixed position relative to the shaft's longitudinal axis 20A, and the distal end of the first linkage 26 can be free to move radially inward toward and outward away from the shaft's longitudinal axis 20A. The first and second linkages 26, 30 can also be connected together in a pivotal relationship, via the linkage bars 32a, 32b, to form the second articulation joint 44. A distal end of the first linkage 26 can be pivotally coupled to proximal ends of each of the linkage bars 32a, 32b at a second pivot point 40 at the second articulation joint 44, and a proximal end of the second linkage 30 can be pivotally coupled to distal ends of each of the linkage bars 32a, 32b at a third pivot point 46 at the second articulation joint 44. The first linkage 26 can thereby be configured to pivot or rotate relative to the second linkage 30, the proximal shaft 24, and the handle 12 about the second pivot point 40, and the second linkage 30 can thereby be configured to pivot or rotate relative to the first linkage 26, the proximal shaft 24, and the handle 12 about the third pivot point 46. The second and third pivot points 40, 46 can each have an axis that is generally perpendicular to the longitudinal axis 20A of the proximal shaft 24. In this way, the first and second linkages 26, 30 can both articulate on a same side of the shaft assembly 20, e.g., on a same side relative to the proximal shaft 24, to allow the end effector 22 to intersect or "cross" the shaft's longitudinal axis 20A. In other words, a longitudinal axis 26A of the first linkage 26 and a longitudinal axis 30A of the second linkage 30 and the end effector 22 can be parallel to the longitudinal axis 20A of the proximal shaft 24 when the articulation assembly 18 is in the straight configuration, as shown in FIGS. 3 and 4. When the articulation assembly 18 is in the articulated configuration, the longitudinal axes 26A, 30A of the first and second linkages 26, 30 can be transverse relative to the shaft's longitudinal axis 20A at first and second angles A1, A2, respectively, to angularly orient the end effector 22. The first and second linkages 26, 30 can be configured to be angularly oriented such that their longitudinal axes 26A, 30A can be substantially perpendicular to one another. The measure of the first and second angles A1, A2 can depend, at least in part, upon the sizes and shapes of the proximal shaft 24, the linkages 26, 30, and the linkage bars 32a, 32b. The angles A1, A2 each being substantially at 0° correspond to the articulation assembly 18 being in the straight configuration. The second and third pivot points 40, 46, can be offset from and positioned a distance apart from the linkages' longitudinal axes 26A, 30A taken along a cross-section of the linkages 26, 30, e.g., offset from center. Such offset pivot point(s) can help guide the first and second linkages 26, 30 in desired articulated directions at the second articulation joint 44.

The proximal shaft 24, the linkages 26, 30, and the linkage bars 32a, 32b can be pivotally coupled together in any way at their associated ones of the pivot points 38, 40, 46, as will be appreciated by a person skilled in the art. As in the illustrated embodiment shown in FIGS. 5-9, a first pin 50 can be inserted, e.g., by press fit, through respective first holes 52 formed in the distal end of the proximal shaft 24 and the proximal end of the first linkage 26 to form a pivot hinge-type joint at the first pivot point 38 between the adjacent proximal shaft 24 and first linkage 26. Similarly, second and third pins 54, 56 can be respectively inserted through second and third holes 58, 60 to pivotally couple the linkage bars 32a, 32b to the first and second linkages 26, 30 at, respectively, the second and third pivot points 40, 46.

The first and second linkages 26, 30 can respectively includes grooves formed therein at the second and third pivot points 40, 46 that can be configured to seat the linkage bars 32a, 32b. By seating the linkage bars 32a, 32b, the grooves can be configured to help reduce the diameter of the device's distal portion including the linkage bars 32a, 32, which can help ease insertion and removal of the device's distal portion to and from a patient's body. However, as in the illustrated embodiment, the linkage bars 32a, 32b can be configured to not be seated flush or sub-flush within the grooves but instead can extend laterally/radially outward from outer surfaces of the first and second linkages 26, 30 such that the shaft's diameter D is larger at the second articulation joint 44 than elsewhere along the shaft's longitudinal length. In one embodiment, the grooves can be configured to define ranges of motion about the second and third pivot points 40, 46.

Figure 5:
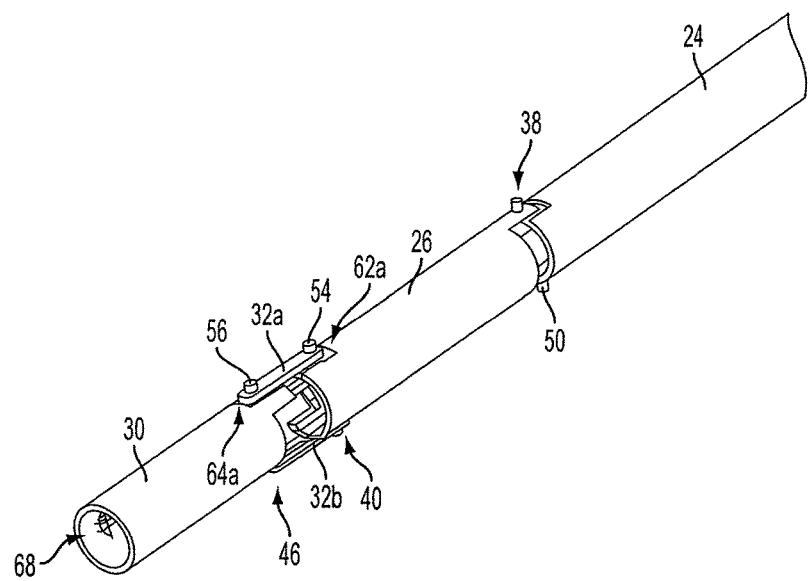
FIG. 5 is a perspective view of a distal portion of the shaft of the device of FIG. 1.
Figure 6:
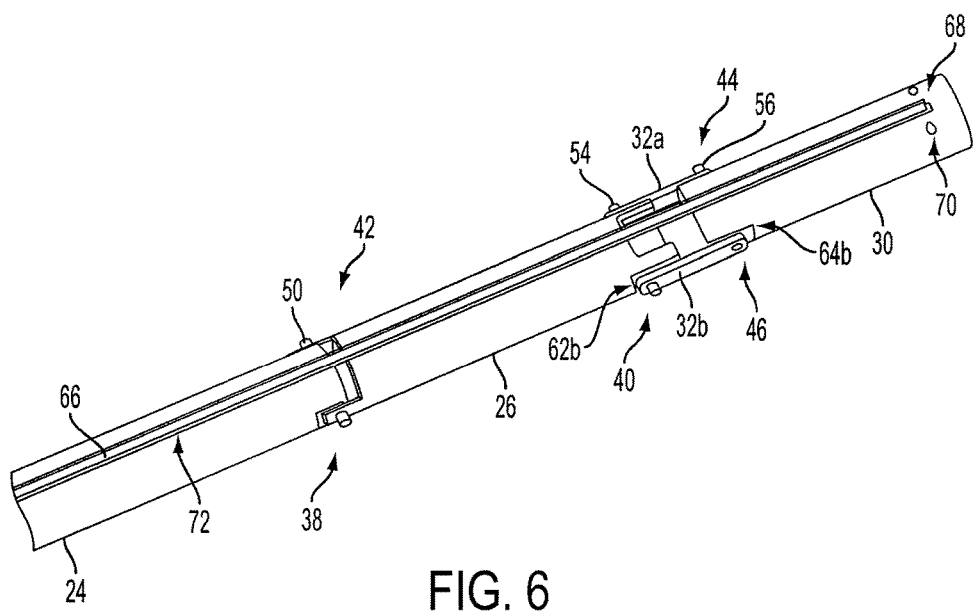
FIG. 6 is another perspective view of a distal portion of the shaft of the device of FIG. 1.
Figure 7:
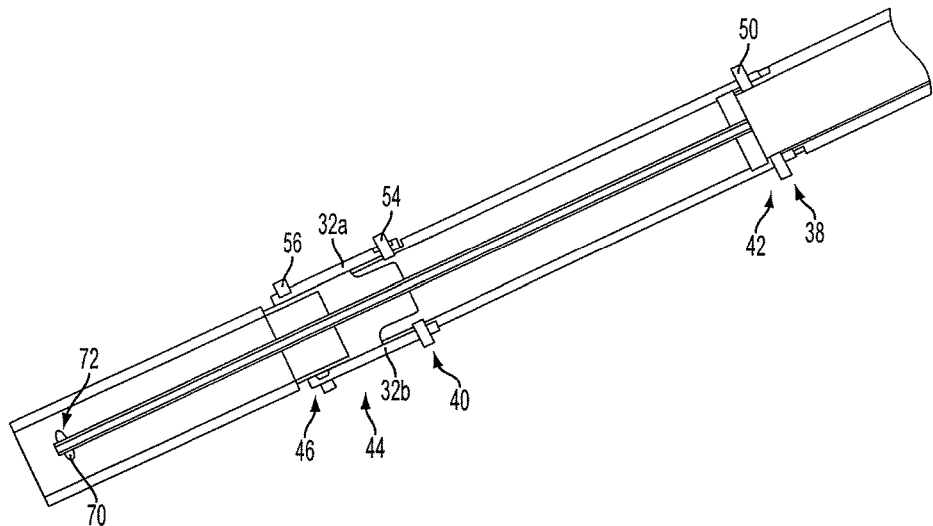
FIG. 7 is a cross-sectional perspective view of the shaft of the device of FIG. 1.
Figure 9:
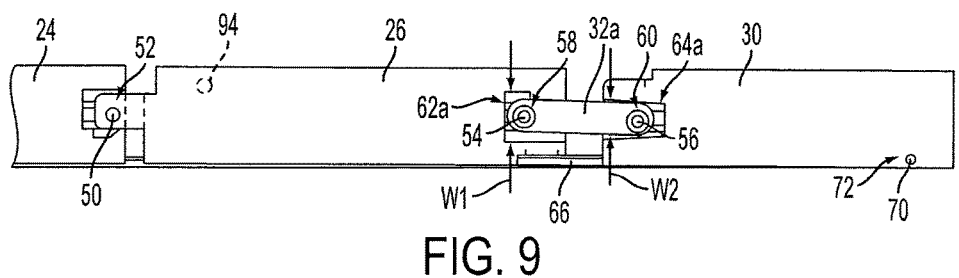
FIG. 9 is a side view of a distal portion of the shaft of the device of FIG. 1.

First and second grooves 62a, 64a seating the first linkage bar 32a, shown in FIGS. 5 and 9, are discussed below in more detail, but as will be appreciated by a person skilled in the art, third and fourth grooves 62b, 64b seating the second linkage bar 32b, shown in FIG. 6, on an opposite side of the shaft assembly 20 can be similarly configured. The first groove 62a formed in the distal end of the first linkage 26 can be configured to seat the proximal end of the first linkage bar 32a, and the second groove 64a formed in the proximal end of the second linkage 30 can be configured to seat the distal end of the first linkage bar 32a. The first and second grooves 62a, 64a can have any size and shape that allow the respective proximal and distal ends of the first linkage bar 32a to be seated therein. In an exemplary embodiment, a maximum width W1 of the first groove 62a can be larger than a maximum width W2 of the second groove 64a, where the widths W1, W2 are measured perpendicular to the shaft's longitudinal axis 20A when the articulation assembly 18 is in the straight configuration, as illustrated in FIG. 9. Such relative sizing of the first and second grooves 62a, 64a can allow the first linkage bar 32a to have a first range of motion about the second pivot point 40 located within the first groove 62a that is more than a second range of motion of the first linkage bar 32a about the third pivot point 46 located within the second groove 64a. In this way, the first linkage bar 32a can be free to move between a first position generally aligned with or parallel to the first and second linkages' longitudinal axes 26A, 30A when the articulation assembly 18 is in the straight configuration, as illustrated in FIG. 9, and to a second, different position angularly oriented relative to the first linkage's longitudinal axis 26A when the articulation assembly 18 is in the articulated configuration, as illustrated in FIG. 8. When the articulation assembly 18 has been articulated to a maximum extent, such as shown in FIG. 8, the first groove 62a can allow the first linkage bar 32a to pivot to be generally aligned with or parallel to the second linkage's longitudinal axis 30A. The maximum width W1 of the first groove 62a can define the first range of motion of the first linkage bar 32a relative to the shaft's axis 20A and hence also a maximum possible degree value of the second angle A2 and a range of motion for the second linkage 30 and the end effector 22. A person skilled in the art will appreciate that relative ranges of motions of the first and second linkage bars 32a, 32b about the second and third pivot points 40, 46 can be achieved using the grooves 62a, 62b, 64a, 64b and/or in other ways, e.g., by providing linkages or linkage bars of different relative longitudinal lengths, by providing a stop element such as a protrusion extending radially outward from a sidewall of one or both of the first and second linkages 26, 30 to prevent rotation of the linkage bars 32a, 32b beyond a certain point, etc. A person skilled in the art will also appreciate that the device 10 can lack any or all of the grooves 62a, 62b, 64a, 64b and thus not limit ranges of motion of about the second and third pivot points 40, 46.

Although the end effector 22 can be pivotally coupled to the second linkage's distal end such that it can pivot or articulate relative to the second linkage 30, in the illustrated embodiment, a proximal end of the end effector 22 is non-pivotally coupled to a distal end of the second linkage 30, e.g., welded, snapped, or press fit thereon, which can allow the end effector 22 to articulate with the second linkage 30 relative to the first linkage 26, the proximal shaft 24, and the handle 12. The end effector 22 can additionally or alternatively be configured to be movable relative to the second linkage 30, such as by being rotatable relative thereto and/or by opening and closing the jaws 16a, 16b, as discussed further below.

Although the end effector 22 is removably and replaceably coupled to the second linkage 30 in the device 10 of FIGS. 1-11 (the end effector 22 is omitted for clarity in FIGS. 1, 3-7 and 9) via the tool 19 proximally inserted therein and moved distally beyond the second linkage's distal end, the end effector 22 can be removably and replaceably coupled to the second linkage 30 in any other way, such as by using any attachment element, e.g., complementary threads on the distal end of the shaft and a proximal end of the end effector, as will be appreciated by a person skilled in the art. In this way, different end effectors having different sizes and/or functions can be selectively attached to the device 10.

Figure 12:
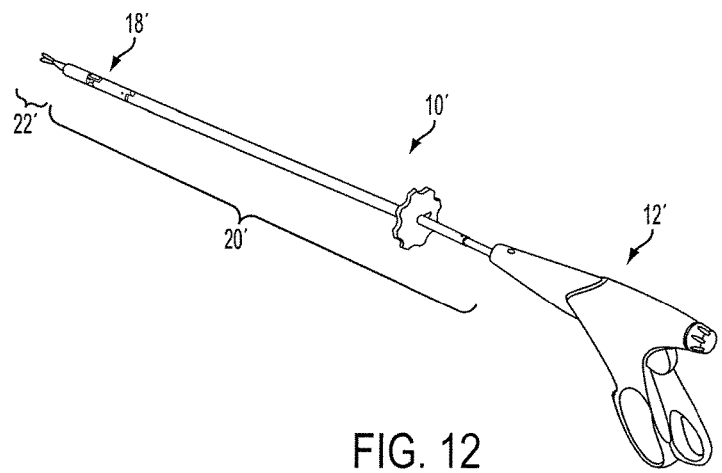
FIG. 12 is a perspective view of one embodiment of a laparoscopic device including a handle and a cannulated articulatable shaft extending distally from the handle, the shaft being in a straight configuration.
Figure 13:
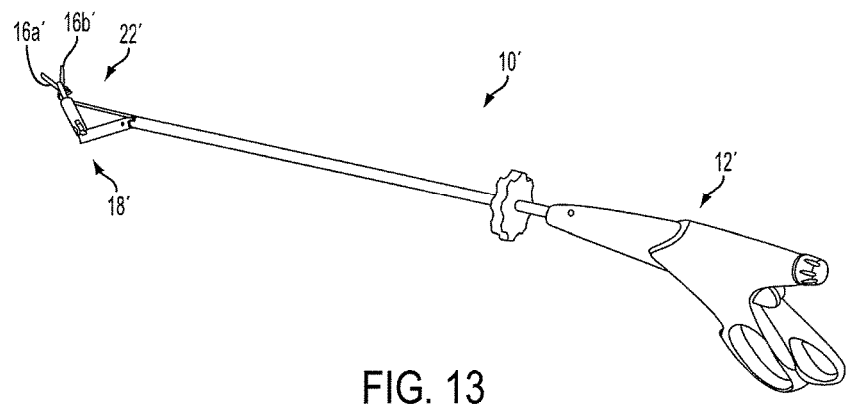
FIG. 13 is a perspective view of one embodiment of a laparoscopic device including a handle and an articulatable shaft extending distally from the handle, the shaft being in an articulated configuration and having an end effector coupled to a distal end thereof.
Figure 14:
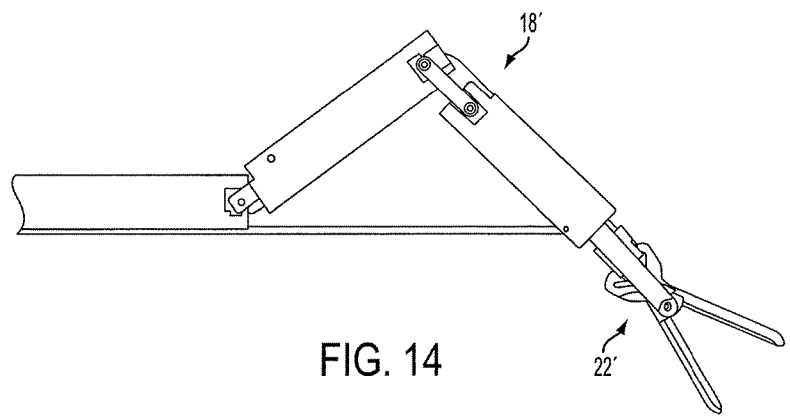
FIG. 14 is a perspective view of a distal portion of the device of FIG. 13.

In one exemplary embodiment, illustrated in FIGS. 12-14, a surgical device 10' is provided that includes a proximal handle 12' having an elongated, tubular shaft assembly 20' extending distally therefrom. The device 10' can be configured and used similar to the device 10 of FIGS. 1-11, but it can have an end effector fixedly attached to a distal end of the shaft assembly 20'. Although, as mentioned above, an end effector can be removably and replaceably coupled to a distal end of the shaft assembly 20' using an attachment element. The end effector 22' is shown in FIGS. 12-14 as a grasper including jaws 16a, 16b, a person skilled in the art will appreciate that any type of end effector can be coupled to the device 10'. Similar to that discussed herein regarding the device 10, an articulation assembly 18' can be configured to articulate the shaft assembly 20' and angularly orient the end effector 22'.

Referring again to the embodiment of FIGS. 1-11, the device 10 can include an articulation actuator configured to articulate the articulation assembly 18 at the first and second articulation joints 42, 44 to form a compound angle. The articulation actuator can have a variety of configurations, but in the illustrated embodiment the articulation actuator includes a rigid, linear or straight rod or bar 66, generally referred to as an "actuator," configured to move relative to the proximal shaft 24 and the two linkages 26, 30 to bend the articulation assembly 18 at the articulation joints 42, 44. Having a rigid articulation actuator can facilitate smooth, controlled articulation of the articulation assembly 18, although the articulation actuator can be flexible or partially flexible, e.g., a flexible cable. The actuator 66 can be solid or can have one or more hollow portions.

As shown in FIGS. 3 and 5-9, the actuator 66 can include a rigid rod having a distal end pivotally coupled to the second linkage 30 at a fourth pivot point 68, and having a proximal end coupled to the device 10 at a location proximal to the first articulation joint 42. The actuator 66 can be pivotally coupled to the second linkage 30 in any way, such as with a pin (not shown) inserted through respective holes 70 formed in the distal end of the actuator 66 and in the second linkage 30. As in the illustrated exemplary embodiment, the fourth pivot point 68 can be located at a distal end of the second linkage 30, which can facilitate controlled articulation and stabilization of the articulation assembly 18. The actuator's proximal end can be coupled to the device 10 in any way and at any location such that movement of the knob 28 is configured to move the actuator 66. The proximal shaft 24 and linkages 26, 30 can include a channel 72 formed therein that can be configured to movably receive the actuator 66. The channel 72 can extend longitudinally along a full or partial longitudinal length of any of the proximal shaft 24 and linkages 26, 30. Although the channel 72 extends along all of the proximal shaft 24 and the linkages 26, 30 in the illustrated embodiment, the channel 72 can extend along only a portion of the shaft assembly 20, e.g., only along the proximal shaft 24. By being configured to seat the actuator 66 such that the actuator 66 sits flush or sub-flush therein, the channel 72 can be configured to help reduce a diameter of the shaft assembly 20, which can help ease insertion and removal of the device's distal portion to and from a patient's body. Although the actuator 66 in the illustrated embodiment includes a single rod, a person skilled in the art will appreciate that the actuator 66 can include multiple rods.

The actuator 66 can extend longitudinally parallel to the longitudinal axis 20A when the articulation assembly 18 is not articulated, but a longitudinal axis 66A of the actuator 66 can be offset from and be parallel to the shaft's longitudinal axis 20A, as shown in FIG. 8. Having such an offset longitudinal axis 66A can reduce clutter in the shaft's lumen 34 and can facilitate articulation of the articulation assembly 18.

As mentioned above, the actuator 66 can be movable relative to the proximal shaft 24. As in the illustrated embodiment, the actuator 66 can be movable longitudinally in proximal and distal directions parallel to the shaft's longitudinal axis 20A to articulate the articulation assembly 18. In response to selective movement of the control knob 28, the actuator 66 can be configured to move longitudinally relative to the shaft's longitudinal axis 20A, e.g., along the actuator's longitudinal axis 66A parallel to the shaft's longitudinal axis 20A. More particularly, when the articulation assembly 18 is in the straight configuration, or when it is not maximally articulated in the articulated configuration, longitudinal movement of the control knob 28 along the shaft's longitudinal axis 20A in a proximal direction can move the proximal shaft 24 longitudinally in a proximal direction over the shaft 36, and it can move the actuator 66 longitudinally in a proximal direction, thereby pulling the distal end of the second linkage 30 proximally to pivot the second linkage 30 relative to the actuator 66 at the fourth pivot point 68. Although the actuator 66 and the second linkage 30 can be pivotally coupled together at the fourth pivot point 38, the distal end of the second linkage 30 can be constrained to longitudinal movement along the longitudinal axis 66A of the actuator 66, and thus parallel to the shaft's longitudinal axis 20A, as the actuator 66 moves proximally and distally, as shown in FIG. 8. Such constrained movement can facilitate controlled, predictable movement of the second linkage 30 and hence of the end effector 22 coupled to the distal end thereof. The pivotal movement of the second linkage 30 about the fourth pivot point 68 can translate motion to the first pivot point 38 at the first articulation joint 42 and to the second and third pivot points 40, 46 at the second articulation joint 44 to form a compound angle.

The articulation assembly 18 can be similarly straightened using the actuator 66. When the articulation assembly 18 is in the articulated configuration, longitudinal movement of the control knob 28 along the shaft's longitudinal axis 20A in a distal direction can distally, longitudinally move the proximal shaft 24 over the shaft 36 and distally, longitudinally move the actuator 66, thereby pivoting the second linkage 30 relative to the actuator 66 at the fourth pivot point 68. The pivotal movement of the second linkage 30 about the fourth pivot point 68 can translate motion to the first and second articulation joints 42, 44 to decrease the compound angle, if not move the articulation assembly 18 from the articulated configuration to the straight configuration.

With the actuator 66 coupled to the distal end of the second linkage 30, the articulation assembly 18 can be bent in a distal-to-proximal direction whether it is being increased or decreased in amount of articulation. In other words, longitudinal movement of the actuator 66 can cause the second linkage 30 to pivot about the third pivot point 46 prior to the first linkage 26 pivoting about the second pivot point 40, and it can cause the first linkage 26 to pivot about the second pivot point 40 prior to the first linkage 26 pivoting about the first pivot point 38.

The articulation actuator can optionally include a second actuator (not shown) configured to further facilitate articulation at the first articulation joint 42. The second actuator can have a distal end coupled to the proximal end of the first linkage 26, e.g., at a coupling point 94 shown in FIG. 9, and it can have a proximal end coupled to the device 10 at a location proximal to the first articulation joint 42. The second actuator can be rigid and/or flexible, although in an exemplary embodiment at least a distal portion of the second actuator can be flexible to allow the second actuator to bend at the first articulation joint 42. In one exemplary embodiment, the second actuator can include a flexible cable extending parallel to the shaft's longitudinal axis 20A within the inner lumen 34, although the second actuator can be positioned outside or partially outside the lumen 34. The second actuator can be configured to be pulled in a proximal direction, such as by manipulating a lever or knob located at the handle 12 or at a proximal portion of the shaft assembly 20, to pull the first linkage 26 at the coupling point 94 and help pivot the first linkage 26 about the first pivot point 38. The second actuator can be coupled to a dedicated lever or knob or to the control knob 28 coupled to the actuator 66. The coupling point 94 can include a fixed coupling point, such as if the second actuator is welded or crimped to the first linkage 26, or can be a movable coupling point, such as with a cam slidably received in a slot formed in the first linkage 26. The coupling point 94 can be laterally/radially offset from the shaft's central longitudinal axis, which in the illustrated embodiment is shown as the longitudinal axis 20A, by being near an outer edge of the first linkage 26, as shown in the embodiment illustrated in FIG. 9. Such an offset position can facilitate movement of the first linkage 26 and changing of the first angle A1 when the second actuator is pulled.

The articulation actuator can be freely longitudinally movable to allow the articulation assembly 18 to articulate any amount at any angles A1, A2. However, the control knob 28 can be configured to be manually held in a fixed position to hold the articulation assembly 18 at a desired compound angle. The device 10 can include a lock configured to mechanically hold the articulation assembly 18 in a fixed position when it is in the articulated configuration, which can ease manipulation of the device 10 when the articulation assembly 18 is articulated. As in the illustrated embodiment, the device 10 can include a lock configured to lock the articulation assembly 18 in a fixed position when it is at a maximum amount of articulation. The lock can have a variety of configurations, as will be appreciated by a person skilled in the art.

Figure 10:
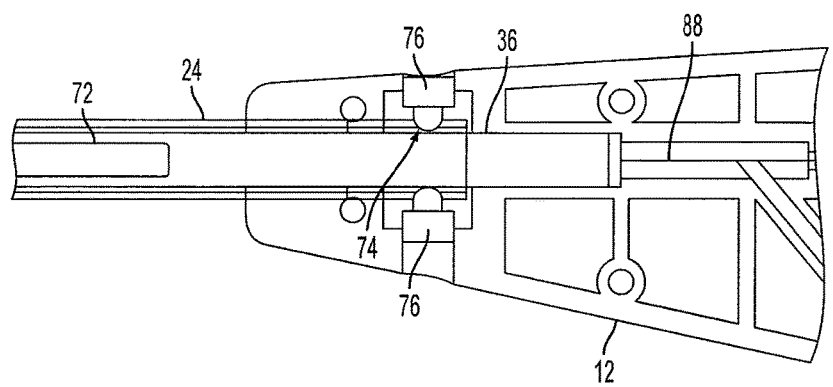
FIG. 10 is a partial, cross-sectional view of the handle and the shaft of the device of FIG. 1.
Figure 11:
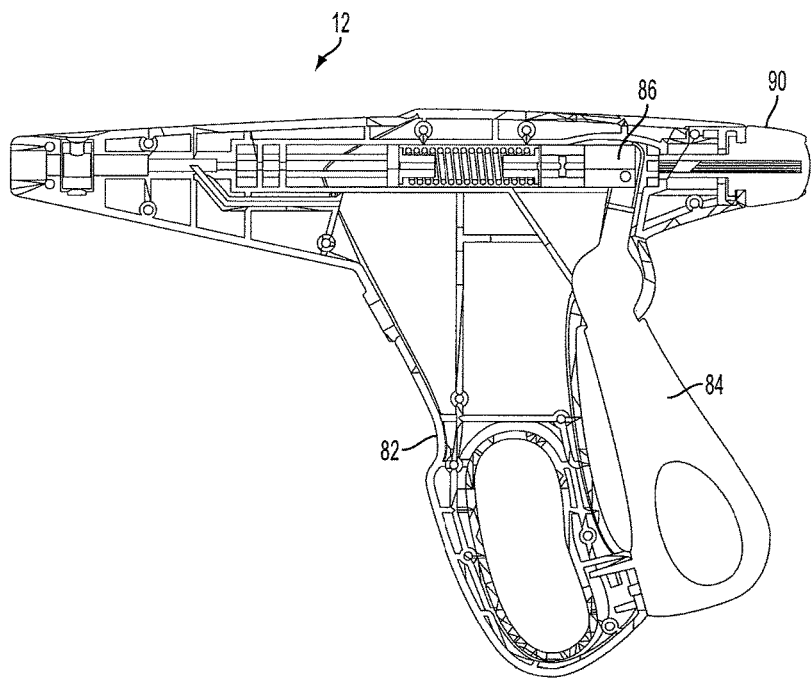
FIG. 11 is a cross-sectional view of the handle of the device of FIG. 1.

In the illustrated embodiment, as shown in FIGS. 2, 3, and 10, the lock includes holes 74 formed in a proximal end of the proximal shaft 24 and complementary pins 76 extending radially inward in a distal portion of the handle 12. The pins 76 can be spring-loaded or otherwise biased to a radially-inward position. Although holes 74 are shown formed in the proximal shaft 24, a person skilled in the art will appreciate that the proximal shaft 24 could instead have depressions or indentations formed therein for receiving the pins 76. A person skilled in the art will also appreciate that although the lock includes two holes 74 and two pins 76, the device's lock can include any number of complementary holes and pins. When the proximal shaft 24 moves a sufficient proximal distance relative to the handle 12, e.g., by pulling the control knob 28 proximally, the holes 74 can align with the pins 76 such that the pins 76 can snap into the holes 74. The engagement of the pins 76 within the holes 74 can hold the proximal shaft 24 in a fixed position relative to the handle 12, thus maintaining the actuator 66 and a remainder of the articulation assembly 18, e.g., the first and second linkages 26, 30, in a fixed position relative to the handle 12 and to each other. The lock can be disengaged in any way, such as by moving the control knob 28 distally to move the proximal shaft 24 distally and thereby snap the pins 76 out of the holes 74.

In addition to being longitudinally movable relative to the handle 12, the control knob 28 can be configured to rotate relative thereto to rotate the shaft assembly 20 about the longitudinal axis 20A. If the end effector 22 is attached to the shaft's distal end, as opposed to being attached to an independent tool inserted through the device such as in the embodiment illustrated in FIGS. 12-14, rotation of the shaft assembly 20 can also rotate the end effector 22. The control knob 28 can be rotatable any amount in clockwise and/or counterclockwise directions. In the illustrated embodiment, the control knob 28 is rotatable 360° in both clockwise and counterclockwise directions when the lock is not engaged, e.g., when the pins 76 are not engaged with the holes 74. When the lock is engaged, the shaft assembly 20 can be prevented from rotating. The proximal shaft 24 can include a plurality of holes 74 arranged radially around its circumference or perimeter to allow the pins 76 to engage holes in the proximal shaft 24 when the proximal shaft 24 is in a variety of rotated orientations.

The control knob 28 can include at least one gripping feature 80, shown in FIG. 1, formed thereon that can be configured to facilitate manipulation of the control knob 28. The gripping feature 80 in the illustrated embodiment includes a plurality of finger depressions around a perimeter of the control knob 28, but a person skilled in the art will appreciate that the control knob 28 can additionally or alternatively include any one or more gripping features, e.g., a textured surface, a finger loop, a non-slip coating, etc.

As mentioned above, the device 10 includes a handle 12 having controls configured to operate the end effector 22, e.g., to actuate and/or rotate the end effector 22. As in the embodiment illustrated in FIGS. 4, 10, and 11, the handle 12 can include an actuator configured to actuate the end effector 22, e.g., to open and close the jaws 16a, 16b. The actuator can have a variety of sizes, shapes, and configurations, but as in the illustrated embodiment, it can include a translator element 88 extending distally from the handle 12, through the shaft 36, and to the end effector 22. The translator element 88 can include an actuator, cable, wire, or rod, generally referred to as a "translator element," shown in FIG. 10, having a proximal end coupled to an activator member in the handle 12 and a distal end coupled to the end effector 22, with a length between the proximal and distal ends extending through the shaft assembly 20. The translator element 88 can include a singular element, e.g., one flexible cable, or it can include multiple elements, e.g., a proximal rigid rod and a distal flexible cable. In an exemplary embodiment, at least a distal portion of the translator element 88 is flexible. By being flexible in at least a distal portion thereof, e.g., in a portion extending through the articulation assembly 18, the translator element 88 can allow for actuation of the end effector 22 and articulation of the articulation assembly 18 at the articulation joints 42, 44. In the illustrated embodiment, the translator element 88 includes a flexible cable. The flexible cable can be formed of any pliable material, e.g., an electroactive polymer, a shape memory material such as Nitinol, etc., and can be attached to the handle 12 and the end effector 22 in any way, e.g., crimped, tied, etc.

The activator member in the handle 12 can vary, but as in the illustrated embodiment, it can include a ratchet 86 driven by a thumb trigger 84. The ratchet 86 can be configured to longitudinally translate the translator element 88 parallel to the longitudinal axis 20A in response to manual pressure on the trigger 84. As the trigger 84 is pivoted relative to a pistol handle grip 82, the trigger 84 ratchets the translator element 88 proximally or distally through the shaft 36, the proximal shaft 24, and the two linkages 26, 30 to move the jaws 16a, 16b, whether the articulation assembly 18 is articulated or not.

As mentioned above, and as will be appreciated by a person skilled in the art, the handle 12 can include any rotating mechanism configured to rotate the end effector 22 before and/or after the articulation assembly 18 is articulated, such as a knob 90 as shown, a lever, a wired or wireless electronic control, etc. The knob 90 can include at least one gripping feature, e.g., raised ridges 92, configured to facilitate manipulation of the knob 90. The knob 90 can be coupled to the translator element 88 and be configured to rotate the translator element 88 a full 360° clockwise and/or counterclockwise to correspondingly rotate the end effector 22 about the second linkage's longitudinal axis 30A, which as mentioned above is the same as the shaft's longitudinal axis 20A when the articulation assembly 18 is in the straight configuration. The knobs 28, 90 can thus allow for separate, relative rotation between the shaft assembly 20 and the end effector 22. By extending through the shaft assembly 20 whether it is articulated or not, the translator element 88 can allow the end effector 22 to be rotated about the shaft's longitudinal axis 20A relative to the shaft assembly 20 with the articulation assembly 18 in either the straight or articulated configuration.

Figure 15:
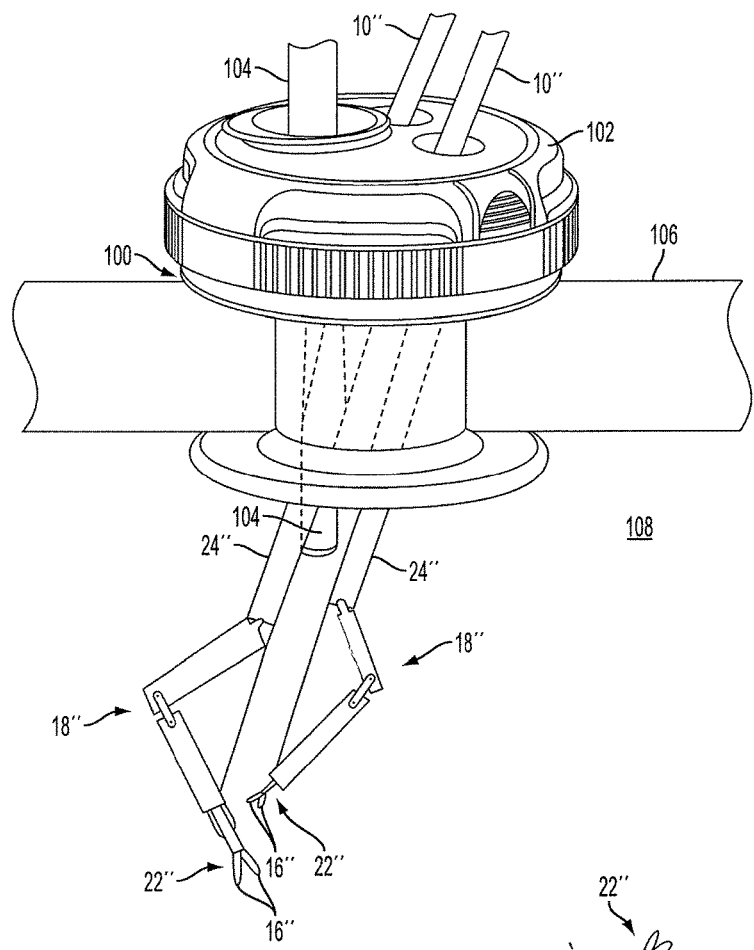
FIG. 15 is a perspective, partially cross-sectional view of a surgical access device positioned within a tissue opening and having two laparoscopic devices and a scoping device inserted therethrough and positioned within a body cavity, the laparoscopic devices each having a shaft in an articulated configuration.

In use, as shown in an exemplary embodiment in FIG. 15, one or more surgical devices 10" can be inserted through an opening 100 in tissue 106 to access a body cavity 108 underlying the tissue 106 where the devices 10" can perform any type of surgical procedure. The devices 10" can generally each be configured and used similar to the device 10 of FIGS. 1-11. As mentioned above, a person skilled in the art will appreciate that while the devices 10" are shown in the illustrated embodiment in use in a laparoscopic procedure and inserted into the body cavity 108, e.g., the abdominal cavity, through a multiple port access device 102 positioned in the tissue opening 100, e.g., an incision at the navel, any of the surgical devices disclosed herein can be used in a variety of surgical procedures and inserted into a patient's body in any number of ways. Prior to insertion of any instruments through the multiple port access device 102, insufflation can be provided through an insufflation port, as will be appreciated by a person skilled in the art. A scoping device 104 can also be inserted through the multiple port access device 102 to provide visualization. Non-limiting examples of a scoping device include an endoscope, a laparoscope, and a colonoscope.

The multiple port access device 102 can include multiple instrument openings each configured to receive an instrument inserted therethrough. Each opening can have an associated sealing port that can be configured to provide at least one instrument seal that forms a seal around an instrument disposed therethrough, but otherwise does not form a seal when no instrument is disposed therethrough, at least one channel seal or zero-closure seal that seals a working channel created by the sealing port when no instrument is disposed therethrough, or a combination instrument seal and channel seal that is effective to both form a seal around an instrument disposed therethrough and to form a seal in the working channel when no instrument is disposed therethrough. Exemplary embodiments of multiple port access devices are described in more detail in U.S. patent application Ser. No. 12/399,482 filed Mar. 6, 2009 entitled "Methods And Devices For Providing Access Into A Body Cavity," U.S. patent application Ser. No. 12/399,473 filed Mar. 6, 2009 entitled "Methods And Devices For Providing Access Into A Body Cavity," U.S. patent application Ser. No. 12/512,542 filed Jul. 30, 2009 entitled "Methods And Devices For Providing Access Into A Body Cavity," U.S. patent application Ser. No. 12/512,568 filed Jul. 30, 2009 entitled "Methods And Devices For Providing Access Into A Body Cavity," U.S. patent application Ser. No. 12/399,633 filed Mar. 6, 2009 entitled "Methods And Devices For Providing Access Into A Body Cavity," U.S. patent application Ser. No. 12/399,625 filed Mar. 6, 2009 entitled "Methods And Devices For Providing Access Into A Body Cavity," U.S. patent application Ser. No. 12/399,547 filed Mar. 6, 2009 entitled "Surgical Access Devices And Methods Providing Seal Movement In Predefined Paths," U.S. patent application Ser. No. 12/399,656 filed Mar. 6, 2009 entitled "Surgical Access Devices And Methods Providing Seal Movement In Predefined Movement Regions," and U.S. patent application Ser. No. 12/766,086 filed Apr. 23, 2010 entitled "Methods And Devices For Accessing A Body Cavity," which are hereby incorporated by reference in their entireties.

The devices 10" can be simultaneously or sequentially inserted through the multiple port access device 102 with the articulation assemblies 18" in straight configurations to position distal portions of the devices' proximal shafts 24" within the body cavity 108. The proximal shafts 24" inserted through the multiple port access device 102 can each extend generally parallel to one another, e.g., have parallel longitudinal axes. If one or both of the end effectors 22" are not already coupled to the devices 10", e.g., if the end effector is located at a distal end of a separate tool not yet inserted through the articulation assembly, the tool can be inserted therethrough to position the end effector(s) 22" distal to the articulation assembly or assemblies 18". Such separate tools having end effectors at distal ends thereof can be inserted after the articulation assemblies 18" have been articulated, but it can be easier and faster to articulate the tools with the articulation assemblies 18" rather than navigate the tools through previously-articulated articulation assemblies 18".

Figure 16:
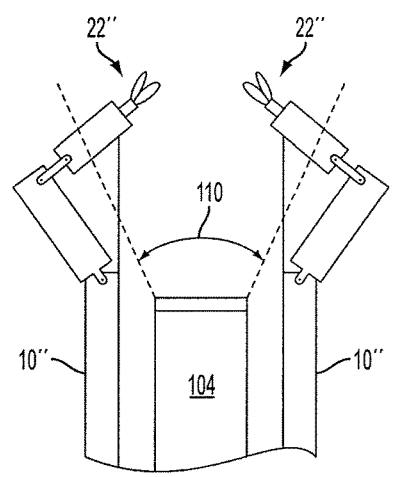
FIG. 16 is a side view of distal portions of the laparoscopic devices and the scoping device of FIG. 15 positioned in the body cavity.

After the distal portions of the proximal shafts 24" and the end effector 22" have been positioned within the body cavity 108, control knobs (not shown) of the devices 10" can be manipulated, simultaneously or sequentially, to move the articulation assemblies 18" from straight configurations to articulated configurations and to allow the end effectors 22" to be brought together in a non-interfering, cooperative, facing relationship and to be within a viewing range 110 of the scoping device 104, as illustrated in FIG. 16. In this way, the proximal shafts 24" of the devices 10" can each extend generally parallel to one another while the articulation assemblies 18" are articulated such that the end effectors 22" can be angularly oriented toward a same target tissue and/or toward one another in a cooperative relationship. The devices' handles (not shown) coupled to proximal ends of the proximal shafts 24" can thus be more easily manipulated outside the body, e.g., with a reduced "chopstick" effect. The devices' articulation assemblies 18" can be articulated any amount, including not at all, same or different from one another, and can be selectively adjusted during the surgical procedure to form larger or smaller compound angles as desired. The devices' shafts can also be rotated relative to the devices' handles, the end effectors 22" can be rotated relative to their respective device shafts, and the end effectors' jaws 16" can be opened and closed. The devices 10" can thus allow the articulation assemblies 18" to be easily inserted into a body in straight configurations through a single, relatively small opening 100 and be subsequently articulated to optimally position the end effectors 22" relative to the surgical site, to each other, to the scoping device 104, and to any other tools within the body cavity 108. Because the device 10" can be articulated, its end effector 22" can be positioned at an angle with respect to a remainder of the proximal shaft 24" thereof, triangulation and visualization can be improved. In other words, even though the devices 10" and the scoping device 104 are inserted through a common incision, it is still possible to see the end effectors 22" of the devices 10" and to bring the end effectors 22" of the two instruments devices 10" together in a facing relationship at a single point within the body cavity 108.

The devices 10" can also be easily removed from the patient's body by moving the articulation assemblies 18" from articulated configurations to straight configurations. The multiple port access device 102 can be configured to allow further adjustment of instruments inserted therethrough, such as by allowing collective rotation of the instruments around a central axis of the multiple port access device 102.

A proximal housing portion of the multiple port access device 102 can be configured to be removable from a distal retractor portion of the multiple port access device 102. Thus, at any point before, during, or after a surgical procedure, the proximal housing portion can in full or part be released from the distal retractor portion, and the distal retractor portion can be removed from the tissue 106. With the proximal housing portion of the multiple port access device 102 disengaged from the distal retractor portion and with the distal retractor portion still positioned in the tissue opening 100, a working channel of the distal retractor portion can provide access to the body cavity 108 underlying the tissue 106. One or more of the devices 10" and/or other surgical instruments can be advanced through the working channel, such as a waste removal bag configured to hold waste material, e.g., dissected tissue, excess fluid, etc., from the body cavity 108. The bag can be introduced into the body cavity 108 through the distal retractor portion's working channel or other access port. A person skilled in the art will appreciate that one or more surgical instruments can be advanced through the distal retractor portion's working channel before and/or after the proximal housing portion has been attached to the distal retractor portion. A surgical drape can optionally be placed over the distal retractor portion and the tissue opening 100 during removal of the distal retractor portion to help reduce dispersion of bodily fluid outside the surgical space.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination, e.g., an end effector, a proximal housing portion of a surgical access device, an end effector, etc. Upon cleaning and/or replacement of particular parts, the device can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Preferably, the invention described herein will be processed before surgery. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high-energy electrons. The radiation kills bacteria on the instrument and in the container. The sterilized instrument can then be stored in the sterile container. The sealed container keeps the instrument sterile until it is opened in the medical facility.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A method for laparoscopic surgery, comprising:
    inserting an end effector of a tool into a body cavity, the tool having a first linkage coupled to an elongate shaft at a first joint, a second linkage having a proximal end coupled to the first linkage at a second joint that is movable away from a central longitudinal axis of the elongate shaft, and an end effector coupled to and inserted through a distal end of the second linkage; and
    actuating the tool to cause the distal end of the second linkage to move parallel to the central longitudinal axis of the elongate shaft.

2. The method of claim 1, wherein actuating the tool causes the second joint to move away from the central longitudinal axis of the elongate shaft.

3. The method of claim 1, wherein actuating the tool causes the first linkage and the second linkage to move from a first position in which the linkages are co-axial with one another to a second position in which the linkages form an angle with each other such that they are no longer co-axial.

4. The method of claim 1, wherein actuating the tool causes an actuator to move longitudinally relative to the central longitudinal axis.

5. The method of claim 1, wherein actuating the tool causes the second linkage to pivot about a pivot point at which an actuator is coupled to the distal end of the second linkage.

6. The method of claim 1, wherein actuating the tool causes the second joint to move radially away from the central longitudinal axis of the elongate shaft.

7. The method of claim 1, further comprising locking the first linkage, second linkage, and end effector in a fixed position relative to the elongate shaft.

8. The method of claim 1, further comprising actuating the tool to move opposed jaws of the end effector of the tool between a closed position and an open position.

9. A method for laparoscopic surgery, comprising:
    inserting a first tool through a first port formed in a housing disposed within tissue to position a first end effector on a distal end of the first tool within a body cavity;
    inserting a second tool through a second port formed in the housing to position a second end effector on a distal end of the second tool within the body cavity;
    longitudinally moving a first actuator extending along a first elongate shaft of the first tool to cause a first linkage and a second linkage on the first end effector to form a compound angle; and
    longitudinally moving a second actuator extending along a second elongate shaft of the second tool to cause a third linkage and a fourth linkage on the second end effector to form a compound angle;
    wherein, when proximal portions of each of the first and second tools are substantially parallel, actuating the first and second tools causes the first and second end effectors to be oriented toward one another without causing the first and second end effectors to intersect.

10. The method of claim 9, further comprising engaging a lock of at least one of the first and second tools to maintain the compound angle of the one of the first and second tools in a fixed position.

11. The method of claim 9, further comprising actuating the first tool to move opposed jaws of the first end effector between a closed position and an open position, wherein the formed compound angle of the first tool remains fixed during actuation of the first tool.

12. The method of claim 9, wherein actuating the first tool causes the first end effector to pivot about a first pivot point along a first longitudinal axis of the first elongate shaft, and actuating the second tool causes the second end effector to pivot about a second pivot point along a second longitudinal axis of the second elongate shaft.

13. The method of claim 9, wherein a distal end of the second linkage of the first tool is constrained to movement along an axis of an actuator that causes the first end effector to form a compound angle, and a distal end of the fourth linkage of the second tool is constrained to movement along an axis of an actuator that causes the second end effector to form a compound angle.

14. The method of claim 9, wherein the first elongate shaft and at least a portion of the first and second linkages includes a channel formed therein that movably receives the first actuator.

* * * * *